(12) United States Patent
Kinomoto et al.

(10) Patent No.: US 11,877,891 B2
(45) Date of Patent: Jan. 23, 2024

(54) ULTRASOUND BRONCHOSCOPE

(71) Applicant: FUJIFILM Corporation, Tokyo (JP)

(72) Inventors: Noboru Kinomoto, Ashigarakami-gun (JP); Yasuhiko Morimoto, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 173 days.

(21) Appl. No.: 17/381,369

(22) Filed: Jul. 21, 2021

(65) Prior Publication Data

US 2022/0071476 A1    Mar. 10, 2022

(30) Foreign Application Priority Data

Sep. 8, 2020   (JP) .................................. 2020-150290

(51) Int. Cl.
*A61B 1/005*    (2006.01)
*A61B 1/267*    (2006.01)
(Continued)

(52) U.S. Cl.
CPC ............ *A61B 8/445* (2013.01); *A61B 8/4483* (2013.01); *A61B 8/56* (2013.01); *A61B 8/12* (2013.01)

(58) Field of Classification Search
CPC ......... A61B 8/445; A61B 8/4483; A61B 8/56; A61B 8/12; A61B 1/0005; A61B 8/42; A61B 8/44
See application file for complete search history.

(56) References Cited

U.S. PATENT DOCUMENTS

| 5,834,699 A | 11/1998 | Buck et al. |
| 2001/0041839 A1 | 11/2001 | Ohara et al. |

(Continued)

FOREIGN PATENT DOCUMENTS

| DE | 10122711 A1 * | 11/2001 | ......... A61B 1/00082 |
| JP | 9-231837 A | 9/1997 | |

(Continued)

OTHER PUBLICATIONS

Japanese Notice of Reasons for Refusal for corresponding Japanese Application No. 2020-150290, dated Apr. 4, 2023, with an English translation.

*Primary Examiner* — Baisakhi Roy
*Assistant Examiner* — Kaitlyn E Sebastian
(74) *Attorney, Agent, or Firm* — Birch, Stewart, Kolasch & Birch, LLP

(57) ABSTRACT

Provided is an ultrasound bronchoscope capable of preventing a non-coaxial cable from being disconnected and improving a degree of freedom of wirings.

An ultrasound bronchoscope includes a distal end part having an ultrasound transducer array, a bending part that is coupled to a proximal end of the distal end part and is bendable in two directions, a flexible part that is coupled to a proximal end of the bending part, a cable that is inserted into the flexible part and the bending part, and a flexible substrate that electrically connects a plurality of ultrasound transducers and the cable, and is disposed over the distal end part, the bending part, and a part of the flexible part. The cable includes a plurality of non-coaxial cables, each non-coaxial cable includes a plurality of signal wires, the distal end part has a structure for regulating a rotation direction of the flexible substrate, such that the flexible substrate is bendable in the same two directions as the bending part, and a plurality of first electrical bonded portions where a plurality of signal wires and a plurality of electrode pads of the flexible substrate are electrically bonded are positioned in a region of the flexible part.

12 Claims, 16 Drawing Sheets

(51) Int. Cl.
*A61B 1/00* (2006.01)
*A61B 8/12* (2006.01)
*A61B 8/00* (2006.01)

(56) References Cited

U.S. PATENT DOCUMENTS

| | | |
|---|---|---|
| 2008/0300492 A1 | 12/2008 | Nagano et al. |
| 2009/0093725 A1* | 4/2009 | Sato ................ H05K 1/147 |
| | | 600/462 |
| 2009/0204006 A1* | 8/2009 | Wakabayashi ......... A61B 8/445 |
| | | 600/463 |
| 2011/0301413 A1 | 12/2011 | Morimoto |
| 2016/0206297 A1 | 7/2016 | Uemichi et al. |
| 2016/0374562 A1 | 12/2016 | Vertikov |
| 2020/0107708 A1 | 4/2020 | Amano |
| 2020/0170621 A1 | 6/2020 | Imahashi |
| 2020/0205777 A1 | 7/2020 | Kumata |

FOREIGN PATENT DOCUMENTS

| | | | |
|---|---|---|---|
| JP | 2001-314404 A | | 11/2001 |
| JP | 2002-153468 A | | 5/2002 |
| JP | 2007-330351 A | | 12/2007 |
| JP | 2008-295749 A | | 12/2008 |
| JP | 2012-16576 A | | 1/2012 |
| JP | 2013-138912 A | | 7/2013 |
| JP | 2015-523868 A | | 8/2015 |
| JP | 5861019 B1 | | 2/2016 |
| JP | 2017045882 A | * | 3/2017 |
| JP | 2019-161 A | | 1/2019 |
| JP | 2019-37304 A | | 3/2019 |
| JP | 2019-54962 A | | 4/2019 |
| WO | WO 2013/154684 A1 | | 10/2013 |
| WO | WO-2018003232 A1 | * | 1/2018 ........... A61B 1/0011 |

* cited by examiner

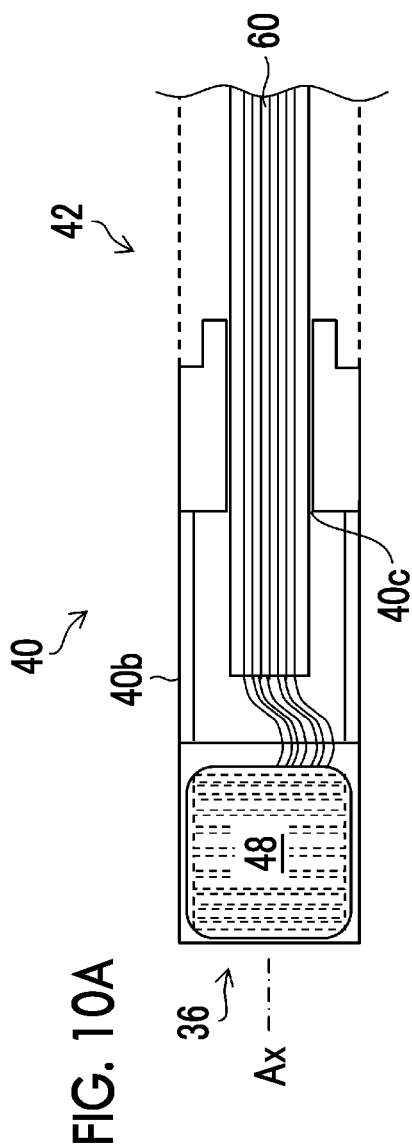
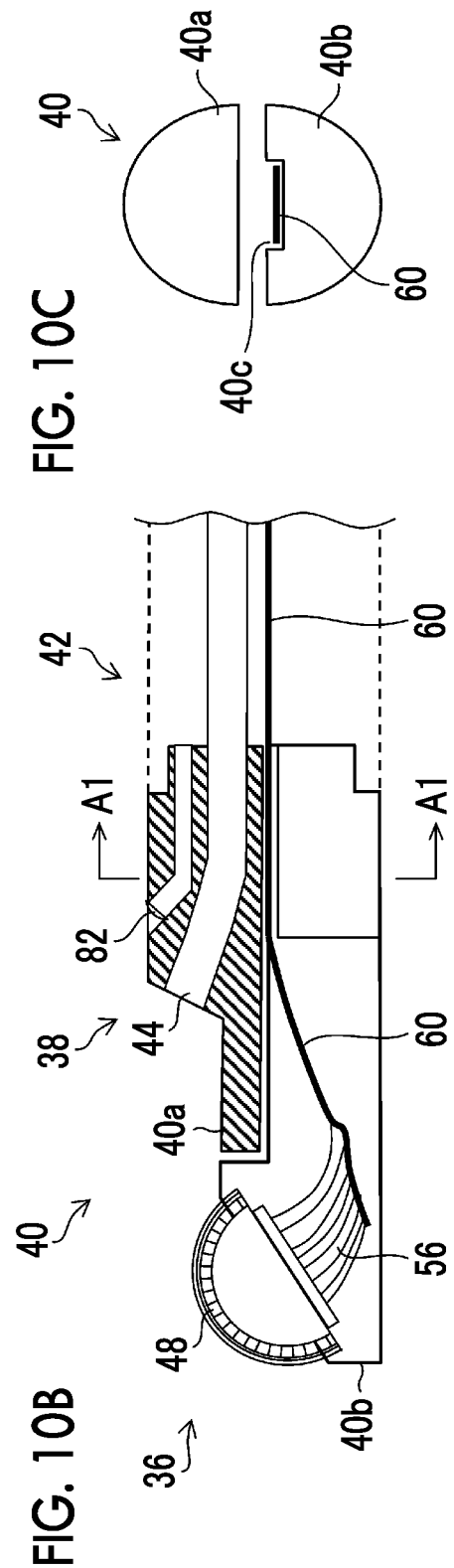
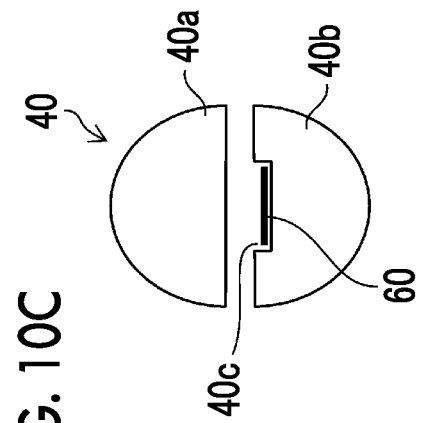

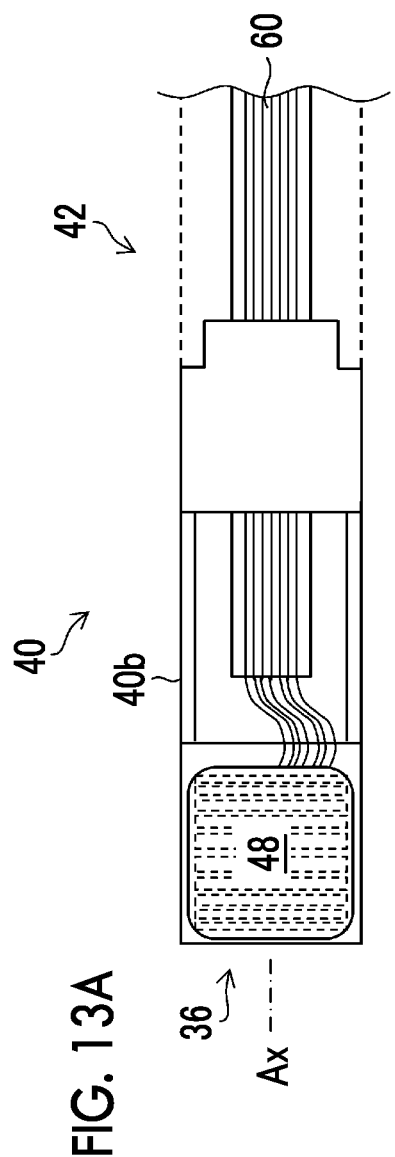
FIG. 13A
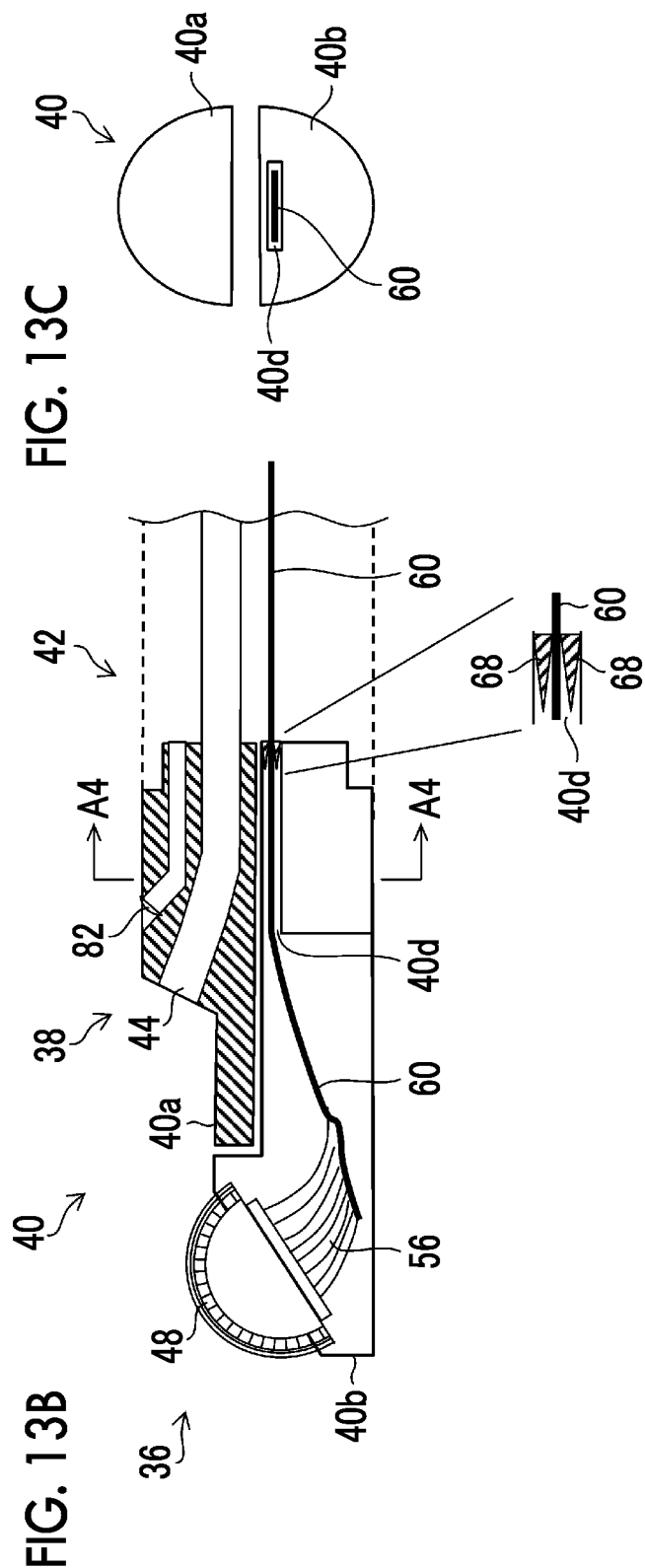
FIG. 13B
FIG. 13C

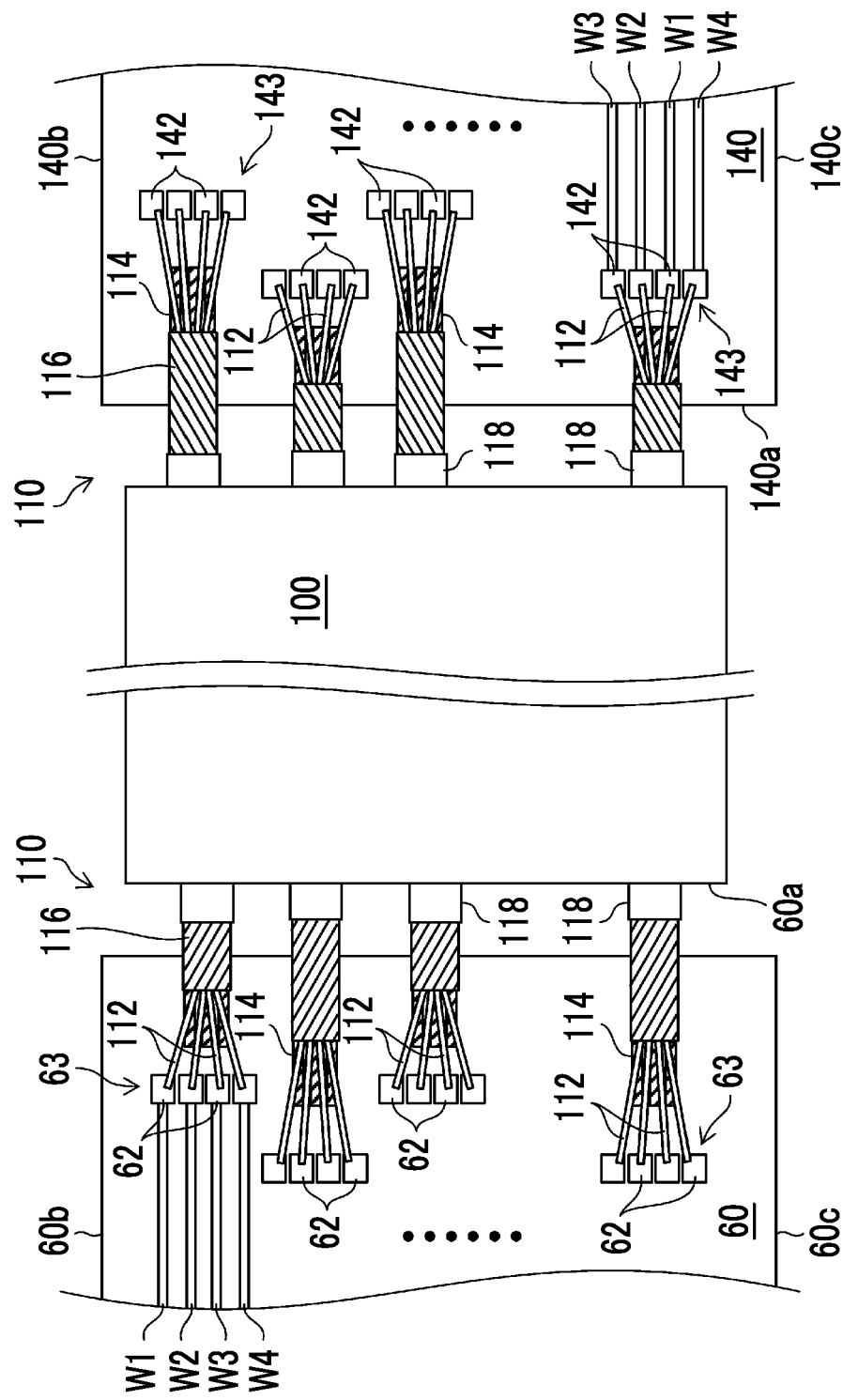

ULTRASOUND BRONCHOSCOPE

CROSS-REFERENCE TO RELATED APPLICATIONS

The present application claims priority under 35 U.S.C § 119 to Japanese Patent Application No. 2020-150290 filed on Sep. 8, 2020. The above application is hereby expressly incorporated by reference, in its entirety, into the present application.

BACKGROUND OF THE INVENTION

1. Field of the Invention

The present invention relates to an ultrasound bronchoscope.

2. Description of the Related Art

In recent years, an ultrasound endoscope that observes a state inside a body of a subject by irradiating the inside of the body with ultrasonic waves and receives reflected waves to capture video has been used in medical practice.

For example, as disclosed in JP2019-054962A, such an ultrasound endoscope comprises a distal end part that comprises piezoelectric elements configuring ultrasound transducers, a bending part and a flexible part connected to a proximal end of the distal end part, a plurality of coaxial cables that are inserted into the bending part and the flexible part, and a flexible substrate that is disposed in the distal end part to electrically connect the piezoelectric elements and the coaxial cable.

SUMMARY OF THE INVENTION

Incidentally, the coaxial cable is configured by covering the periphery of one signal wire coated for insulation with a shield layer and an outer coat. For this reason, the outside diameter of the coaxial cable increases, and the ultrasound endoscope, and in particular, an ultrasound bronchoscope is hardly reduced in diameter.

Accordingly, a case where the bronchoscope is reduced in diameter by applying a non-coaxial cable instead of the coaxial cable is considered. However, the non-coaxial cable does not comprise the shield layer and the outer coat for each one signal wire. For this reason, there is a problem in that the non-coaxial cable is likely to be cut at the time of connection to a wiring substrate.

The non-coaxial cable is electrically bonded with a plurality of signal wires as one set. For this reason, there is a problem in that a degree of freedom of wirings in connection to the flexible substrate is low.

The invention has been accomplished in view of such a situation, and an object of the invention is to provide an ultrasound bronchoscope capable of preventing a non-coaxial cable from being cut and improving a degree of freedom of wirings.

An ultrasound bronchoscope of a first aspect comprises a distal end part that has an ultrasound transducer array in which a plurality of ultrasound transducers are arranged, a bending part that is coupled to a proximal end of the distal end part and is bendable in two directions, a flexible part that is coupled to a proximal end of the bending part, a cable that is inserted into the flexible part and the bending part, and a flexible substrate that electrically connects the plurality of ultrasound transducers and the cable, and includes a plurality of electrode pads connected to the plurality of ultrasound transducers, respectively. The cable has a non-coaxial cable that includes a first cable bundle consisting of a plurality of signal wires and a plurality of ground wires, and a first shield layer with which the first cable bundle is coated, and an outer coat with which a second cable bundle consisting of a plurality of the non-coaxial cables is coated. The flexible substrate is disposed over the distal end part, the bending part, and a part of the flexible part, the distal end part has a structure for regulating a rotation direction of the flexible substrate, such that the flexible substrate is bendable in the same two directions as the bending part, each first cable bundle is individually led out from the cable and the signal wires of the first cable bundle are led out and are electrically bonded to the electrode pads to form a plurality of first electrical bonded portions, and the plurality of first electrical bonded portions are positioned in a region of the flexible part.

In an ultrasound bronchoscope of a second aspect, the plurality of first electrical bonded portions are collectively disposed for each first cable bundle, the cable is connected to a connector substrate on a proximal end side, the connector substrate includes connector-side electrode pads corresponding to the signal wires included in the first cable bundle, the connector-side electrode pads and the signal wires are connected to form a plurality of second electrical bonded portions, and the plurality of second electrical bonded portions are collectively disposed for each first cable bundle.

In an ultrasound bronchoscope of a third aspect, the flexible substrate is a multilayer flexible substrate with ground layers respectively provided on both surfaces.

An ultrasound bronchoscope of a fourth aspect further comprises a first insulating member that covers the first electrical bonded portions.

An ultrasound bronchoscope of a fifth aspect further comprises a second insulating member that covers the flexible substrate.

An ultrasound bronchoscope of a sixth aspect further comprises a reinforcing material that protects the first electrical bonded portions.

In an ultrasound bronchoscope of a seventh aspect, the structure is configured with, as the distal end part has a two-split structure of a first distal end member and a second distal end member, the flexible substrate fixed to a groove of the second distal end member by an adhesive, and the first distal end member and the second distal end member that sandwich the flexible substrate.

In an ultrasound bronchoscope of an eighth aspect, the structure is configured with, as the distal end part has a two-split structure of a first distal end member and a second distal end member, the flexible substrate coated with a sealing member and fixed to a groove of the second distal end member by the sealing member, and the first distal end member and the second distal end member that sandwich the flexible substrate.

In an ultrasound bronchoscope of a ninth aspect, the structure is configured with, the distal end part has a two-split structure of a first distal end member and a second distal end member, the flexible substrate fixed to a groove of the second distal end member by an adhesive, and a cover member different from the first distal end member and the second distal end member that sandwich the flexible substrate.

In an ultrasound bronchoscope of a tenth aspect, the structure is configured with, the distal end part has a two-split structure of a first distal end member and a second distal end member, the flexible substrate inserted into a through-hole provided in the second distal end member, and a locking member inserted into a gap with the flexible substrate in the through-hole.

In an ultrasound bronchoscope of an eleventh aspect, the structure is a structure in which, as the distal end part has a two-split structure of a first distal end member and a second distal end member, the flexible substrate is disposed in a groove of the second distal end member, and the flexible substrate is fixed to the second distal end member by a fastening member.

With the ultrasound bronchoscope according to the aspects of the invention, it is possible to prevent a non-coaxial cable from being disconnected and to improve a degree of freedom of wirings.

BRIEF DESCRIPTION OF THE DRAWINGS

FIGS. 10A to 10C are diagrams illustrating a first form of a regulation structure.

FIGS. 12A to 12C are diagrams illustrating a third form of a regulation structure.

FIGS. 13A to 13C are diagrams illustrating a fourth form of a regulation structure.

FIGS. 14A to 14C are diagrams illustrating a fifth form of a regulation structure.

FIG. 15 is a diagram illustrating a connection structure of the cable, the flexible substrate, and a connector substrate.

DESCRIPTION OF THE PREFERRED EMBODIMENTS

Hereinafter, a preferred embodiment of an ultrasound bronchoscope according to the invention will be described referring to the accompanying drawings.

Figure 1:
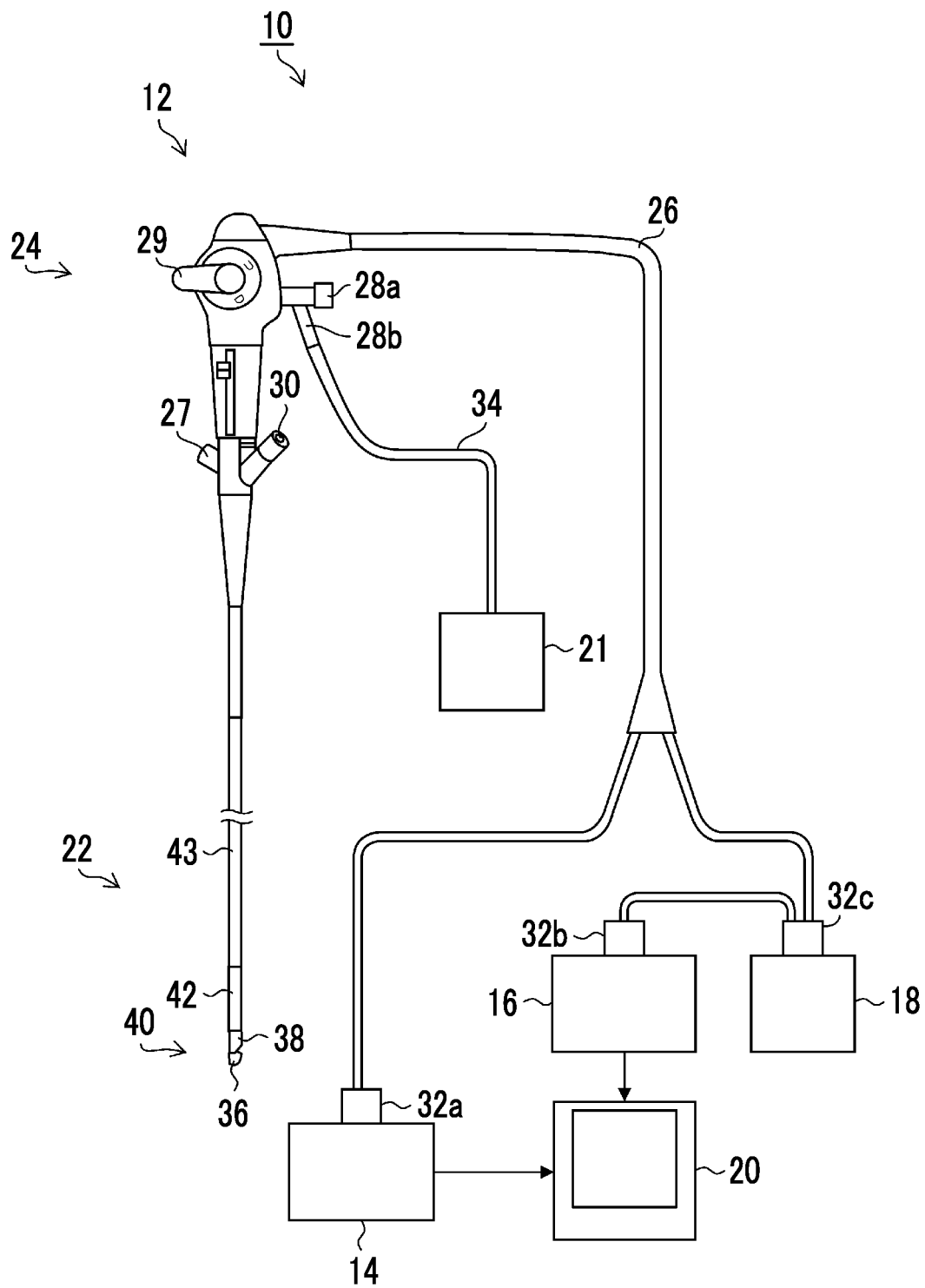
FIG. 1 is a schematic configuration diagram showing an example of the configuration of an ultrasonography system.

FIG. 1 is a schematic configuration diagram showing an example of an ultrasonography system 10 that uses an ultrasound bronchoscope 12 of an embodiment.

As shown in FIG. 1, the ultrasonography system 10 comprises the ultrasound bronchoscope 12, an ultrasound processor device 14 that generates an ultrasound image, an endoscope processor device 16 that generates an endoscope image, a light source device 18 that supplies illumination light, with which the inside of a body cavity is illuminated, to the ultrasound bronchoscope 12, and a monitor 20 that displays the ultrasound image and the endoscope image. The ultrasonography system 10 comprises a suction pump 21 that sucks aspirates.

The ultrasound bronchoscope 12 has an insertion part 22 that is inserted into the body cavity of the subject, an operating part 24 that is consecutively provided in a proximal end portion of the insertion part 22 and is used by an operator to perform an operation, and a universal cord 26 that has one end connected to the operating part 24.

The operating part 24 comprises a suction button 28a, and a suction connector 28b that is opened and closed in conjunction with an operation of the suction button 28a. The suction connector 28b is connected to the suction pump 21 through a suction tube 34. The operating part 24 is provided with a balloon water supply port 27, an angle lever 29, and a treatment tool insertion port 30. In a case where an ultrasound balloon is used, sterilized water can be injected from the balloon water supply port 27 to swell the ultrasound balloon.

In the other end portion of the universal cord 26, an ultrasound connector 32a that is connected to the ultrasound processor device 14, an endoscope connector 32b that is connected to the endoscope processor device 16, and a light source connector 32c that is connected to the light source device 18 are provided. The ultrasound bronchoscope 12 is attachably and detachably connected to the ultrasound processor device 14, the endoscope processor device 16, and the light source device 18 respectively through the connectors 32a, 32b, and 32c.

The insertion part 22 has, in order from a distal end side, a distal end part 40 that has an ultrasound observation part 36 and an endoscope observation part 38, a bending part 42 that is consecutively provided on a proximal end side of the distal end part 40 and is bendable in two directions, and a flexible part 43 that couples a proximal end side of the bending part 42 and the distal end side of the operating part 24.

The bending part 42 is bent and operated in two directions remotely by operating the angle lever 29 provided in the operating part 24. With the operation, the distal end part 40 is directed to a part desired to be observed.

The ultrasound processor device 14 generates and supplies an ultrasound signal for making an ultrasound transducer array 50 of an ultrasound transducer unit 46 (see FIG. 2) of the ultrasound observation part 36 described below generate an ultrasonic wave. The ultrasound processor device 14 receives and acquires an echo signal reflected from an observation target part irradiated with the ultrasonic wave, by the ultrasound transducer array 50 and executes various kinds of signal processing on the acquired echo signal to generate an ultrasound image that is displayed on the monitor 20.

The endoscope processor device 16 receives and acquires a captured image signal acquired from the observation target part illuminated with illumination light from the light source device 18 in the endoscope observation part 38 and execute various kinds of signal processing and image processing on the acquired image signal to generate an endoscope image that is displayed on the monitor 20.

The ultrasound processor device 14 and the endoscope processor device 16 are configured with two devices (computers) provided separately. Note that the invention is not limited thereto, and both the ultrasound processor device 14 and the endoscope processor device 16 may be configured with one device.

To image an observation target part inside a body cavity using the endoscope observation part 38 to acquire an image signal, the light source device 18 generates illumination light, such as white light including light of three primary colors of red light, green light, and blue light or light of a specific wavelength. Light propagates through a light guide (not shown) and the like in the ultrasound bronchoscope 12, and is emitted from the endoscope observation part 38, and the observation target part inside the body cavity is illuminated with light.

The monitor 20 receives video signals generated by the ultrasound processor device 14 and the endoscope processor device 16 and displays an ultrasound image and an endoscope image. In regard to the display of the ultrasound image and the endoscope image, only one image may be appropriately switched and displayed on the monitor 20 or both images may be displayed simultaneously.

In the embodiment, although the ultrasound image and the endoscope image are displayed on one monitor 20, a monitor for ultrasound image display and a monitor for endoscope image display may be provided separately. Alternatively, the ultrasound image and the endoscope image may be displayed in a display form other than the monitor 20, for example, in a form of being displayed on a display of a terminal carried with the operator.

Next, the configuration of the distal end part 40 will be described referring to FIGS. 2 and 3.

Figure 2:
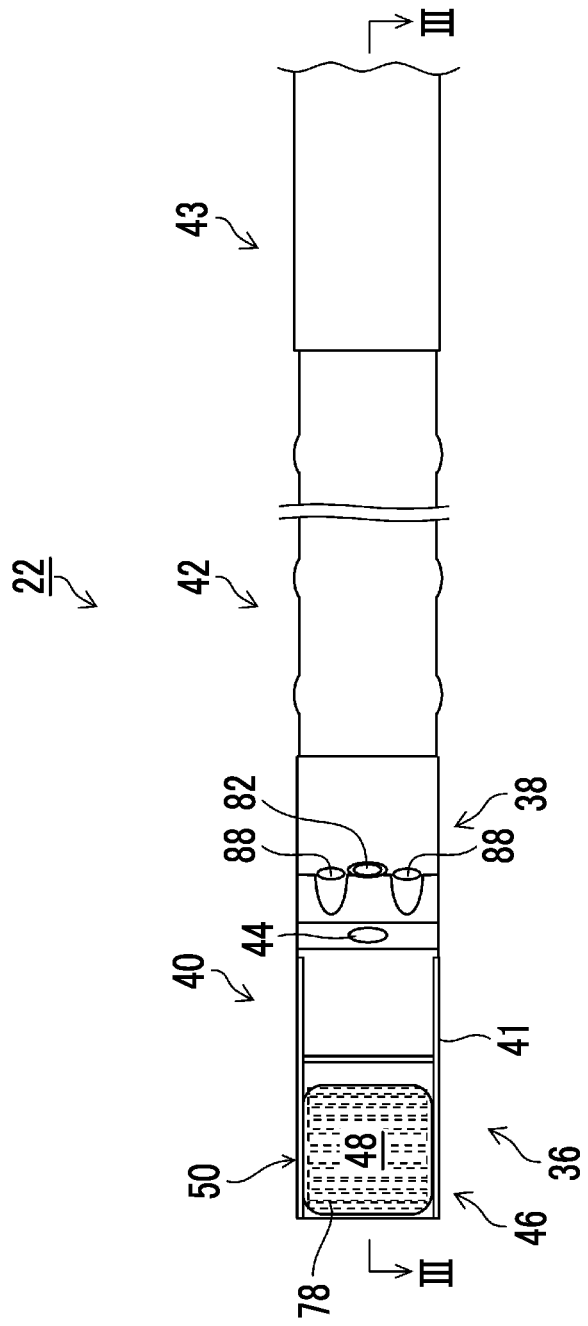
FIG. 2 is a plan view including a distal end part, a bending part, and a part of a flexible part of an ultrasound bronchoscope of FIG. 1.

FIG. 2 is a partial enlarged plan view showing the distal end part 40 shown in FIG. 1 and the vicinity thereof the distal end part 40. FIG. 3 is a cross-sectional view taken along the line shown in FIG. 2, and is a longitudinal sectional view of the distal end part 40 taken along a center line thereof in a longitudinal axis direction.

Figure 3:
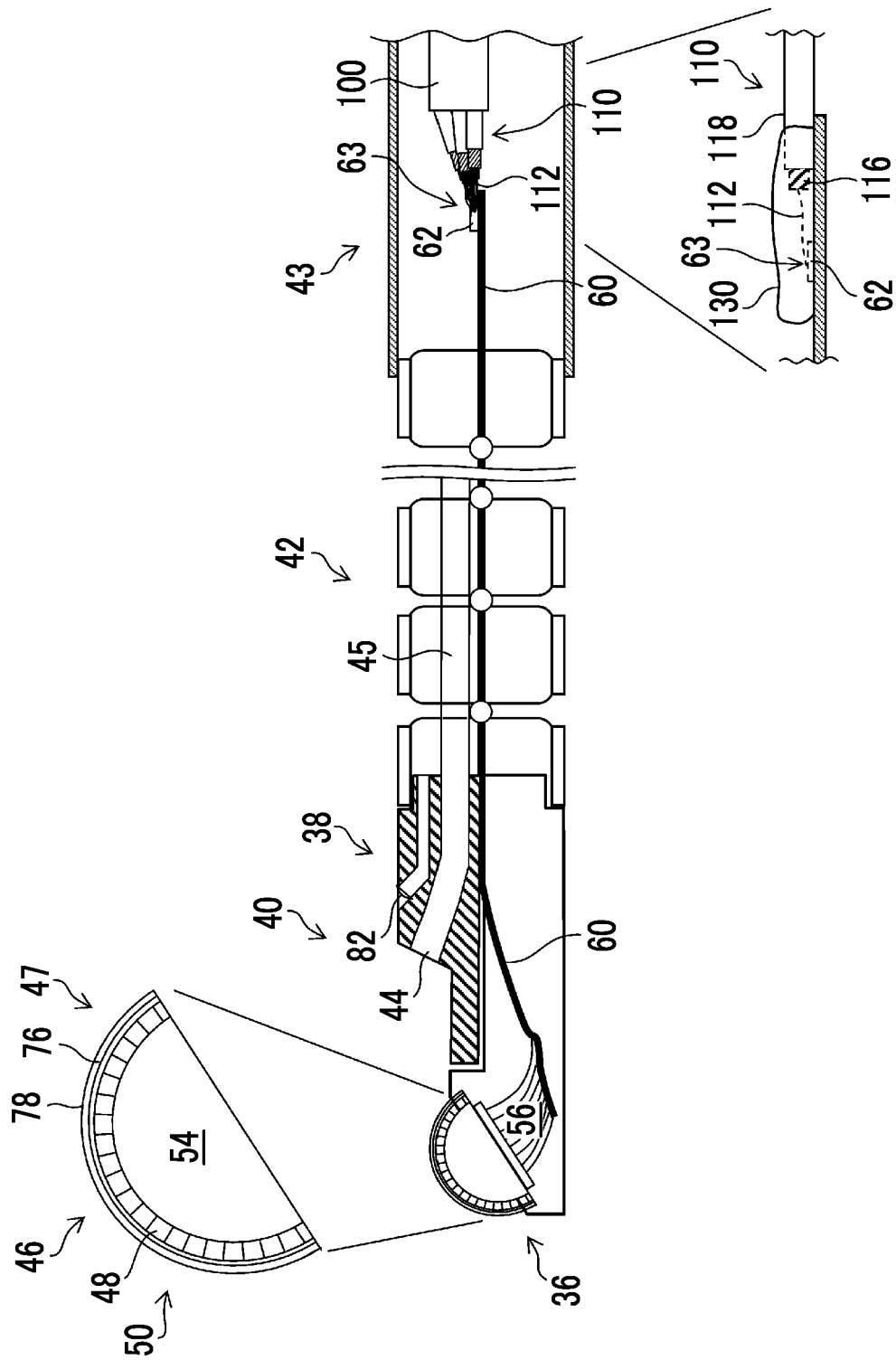
FIG. 3 is a cross-sectional view taken along the line of FIG. 2.

As shown in FIGS. 2 and 3, in the distal end part 40, the ultrasound observation part 36 that acquires an ultrasound image is mounted on the distal end side, and the endoscope observation part 38 that acquires an endoscope image is mounted on the proximal end side. In the distal end part 40, a treatment tool lead-out port 44 is provided between the ultrasound observation part 36 and the endoscope observation part 38.

The endoscope observation part 38 is configured with an observation window 82, illumination windows 88, and the like. In the observation window 82, an objective lens, a solid-state imaging element, and a wiring cable (not shown) are disposed.

The treatment tool lead-out port 44 is connected to a treatment tool channel 45 that is inserted into the insertion part 22. A treatment tool (not shown) inserted from the treatment tool insertion port 30 of FIG. 1 is let out from the treatment tool lead-out port 44 into the body cavity through the treatment tool channel 45.

As shown in FIGS. 2 and 3, the ultrasound observation part 36 comprises the ultrasound transducer unit 46, and an exterior member 41 that holds the ultrasound transducer unit 46.

The ultrasound transducer unit 46 has the ultrasound transducer array 50 that consists of a plurality of ultrasound transducers 48, electrode (not shown) that is provided on an end side of the ultrasound transducer array 50 in a width direction (a direction perpendicular to the longitudinal axis direction of the insertion part 22), a backing material layer 54 that supports each ultrasound transducer 48 from a lower surface side, and a filler layer (not shown) with which an internal space between the exterior member 41 and the backing material layer 54 is filled. The exterior member 41 is made of a rigid member, such as rigid resin, and configures a part of the distal end part 40.

The electrode (not shown) of the ultrasound transducer array 50 has an individual electrode (not shown) that is individually and independently provided for each ultrasound transducer 48, and a transducer ground (not shown) that is a common electrode common to all the ultrasound transducers 48.

The ultrasound transducer unit 46 has an acoustic matching layer 76 laminated on the ultrasound transducer array 50, and an acoustic lens 78 laminated on the acoustic matching layer 76. That is, the ultrasound transducer unit 46 is configured as a laminate 47 having the acoustic lens 78, the acoustic matching layer 76, the ultrasound transducer array 50, and the backing material layer 54.

The ultrasound transducer array 50 is configured with a plurality of rectangular parallelepiped ultrasound transducers 48 arranged in a convex arc shape outward. The ultrasound transducer array 50 is an array of 48 to 192 channels consisting of 48 to 192 ultrasound transducers 48, for example. Each of the ultrasound transducers 48 has a piezoelectric body (not shown).

The electrode of the ultrasound transducer array 50 and a flexible substrate 60 are electrically connected by a plurality of signal wires 56. Electrical bonding of the signal wires 56 and the electrode of the ultrasound transducer array 50 can be established by, for example, a resin material having conductivity. Examples of the resin material include an anisotropic conductive film (ACF) or an anisotropic conductive paste (ACP) obtained by mixing thermosetting resin with fine conductive particles and forming the mixture into a film. As another resin material, for example, a resin material in which a conductive filler, such as metallic particles, is dispersed into binder resin, such as epoxy or urethane, and the filler forms a conductive path after adhesion may be used. Examples of this resin material include a conductive paste, such as a silver paste.

The flexible substrate 60 comprises 48 to 192 signal wirings (not shown) that are electrically connected to the individual electrodes of 48 to 192 ultrasound transducers 48, respectively.

The flexible substrate 60 of the embodiment is disposed over the distal end part 40, the bending part 42, and a part of the flexible part 43. The flexible substrate 60 has a plurality of electrode pads 62 on a proximal end side. A plurality of electrode pads 62 electrically connected to the ultrasound transducers 48 through the signal wirings, respectively.

The flexible substrate 60 is configured in a thin sheet shape in which two principal surfaces face each other, and has flexibility to be bendable. The flexible substrate 60 is disposed in an orientation to be bendable in the same two directions as the bending part 42. The flexible substrate 60 is also referred to as a flexible print substrate (flexible printed circuit (FPC)).

As shown in FIG. 3, a cable 100 includes a plurality of non-coaxial cables 110. Each of the non-coaxial cables 110 includes a first cable bundle 116 covered with a first shield layer 118, and the first cable bundle 116 includes a plurality of signal wires 112. The electrode pads 62 and the signal wires 112 are electrically bonded to form first electrical bonded portions 63. As described below, it is preferable that a reinforcing material 130 is provided in the first electrical bonded portions 63 to protect the first electrical bonded portions 63.

The ultrasound transducer array 50 has a configuration in which a plurality of ultrasound transducers 48 are arranged at a predetermined pitch in a one-dimensional array as an example. The ultrasound transducers 48 configuring the ultrasound transducer array 50 are arranged at regular intervals in a convex bent shape along an axial direction of the distal end part 40 (the longitudinal axis direction of the insertion part 22) and are sequentially driven based on drive signals input from the ultrasound processor device 14 (see FIG. 1). With this, convex electronic scanning is performed with a range where the ultrasound transducers 48 shown in FIG. 2 are arranged, as a scanning range.

The acoustic matching layer 76 is a layer that is provided for taking acoustic impedance matching between the subject and the ultrasound transducers 48.

The acoustic lens 78 is a lens that is provided for converging the ultrasonic waves emitted from the ultrasound transducer array 50 toward the observation target part. The acoustic lens 78 is formed of, for example, silicon-based resin (millable type silicon rubber, liquid silicon rubber, or the lie), butadiene-based resin, or polyurethane-based resin. In the acoustic lens 78, powder, such as titanium oxide, alumina, or silica, is mixed as necessary. With this, the acoustic lens 78 can take acoustic impedance matching between the subject and the ultrasound transducers 48 in the acoustic matching layer 76, and can increase the transmittance of the ultrasonic waves.

As shown in FIG. 3, the backing material layer 54 is disposed on an inside with respect to the arrangement surface of a plurality of ultrasound transducers 48, that is, a rear surface (lower surface) of the ultrasound transducer array 50. The backing material layer 54 is made of a layer of a member made of a backing material. The backing material layer 54 has a role of mechanically and flexibly supporting the ultrasound transducer array 50 and attenuating ultrasonic waves propagated to the backing material layer 54 side among ultrasound signals emitted from a plurality of ultrasound transducers 48 or reflected propagated from the observation target. For this reason, the backing material is made of a material having rigidity, such as hard rubber, and an ultrasonic wave attenuation material (ferrite, ceramics, or the like) is added as needed.

With the ultrasound transducer unit 46 configured as described above, each ultrasound transducer 48 of the ultrasound transducer array 50 is driven. In a case where a voltage is applied to the electrode of the ultrasound transducer 48 through the non-coaxial cable 110 of the cable 100, the wiring of the flexible substrate 60, and the signal wires 56, the piezoelectric body vibrates to sequentially ultrasonic waves, and the irradiation of the ultrasonic waves is performed toward the observation target part of the subject. Then, as a plurality of ultrasound transducers 48 are sequentially driven by an electronic switch, such as a multiplexer, scanning with ultrasonic waves is performed in a scanning range along a curved surface on which the ultrasound transducer array 50 is disposed, for example, a range of about several tens mm from the center of curvature of the curved surface.

In a case where the echo signal reflected from the observation target part is received, the piezoelectric body vibrates to generate a voltage and outputs the voltage as an electric signal corresponding to the received ultrasound echo to the ultrasound processor device 14. Then, the electric signal is subjected to various kinds of signal processing in the ultrasound processor device 14 and is displayed as an ultrasound image on the monitor 20.

Next, a sectional structure of the non-coaxial cable 110 will be described referring to FIG. 4, and next, a sectional structure of the cable 100 will be described referring to FIG. 5. Here, the sectional structure is a structure in sectional view taken along a plane perpendicular to a longitudinal axis direction of the non-coaxial cable 110 and the cable 100.

Figure 4:
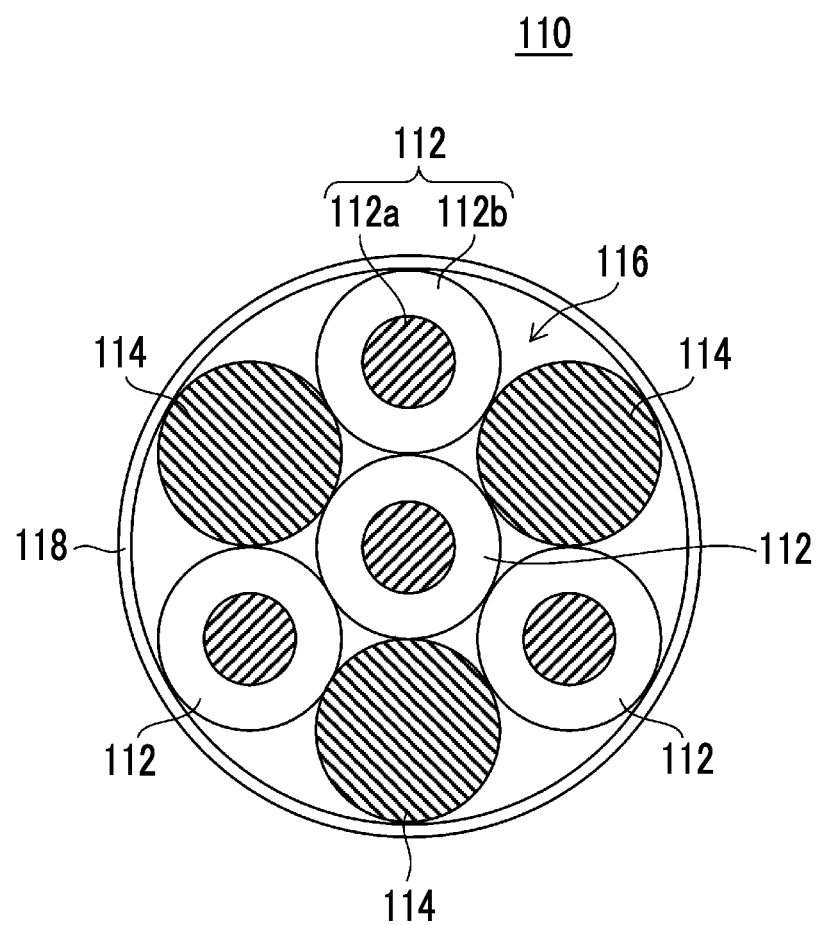
FIG. 4 is a sectional view of a non-coaxial cable.

As shown in FIG. 4, the non-coaxial cable 110 has a plurality of signal wires 112 and a plurality of ground wires 114. Each signal wire 112 is made of, for example, a conductor 112a, and an insulating layer 112b with which the periphery of the conductor 112a is coated. The conductor 112a is made of, for example, an element wire, such as copper or copper alloy. The element wire is subjected to, for example, plating processing, such as tin plating or silver plating. The conductor 112a has a diameter of 0.03 mm to 0.04 mm.

The insulating layer 112b can be made of, for example, a resin material, such as fluorinated-ethylene-propylene (FEP) or perfluoroalkoxy (PFA). The insulating layer 112b has a thickness of 0.015 mm to 0.025 mm.

Each ground wire 114 is made of a conductor having the same diameter as the signal wire 112. The ground wire 114 is made of an element wire, such as copper or copper alloy, or a stranded wire obtained by stranding a plurality of element wires, such as copper or copper alloy.

A first cable bundle 116 is configured by stranding a plurality of signal wires 112 and a plurality of ground wires 114.

Each non-coaxial cable 110 comprises a first shield layer 118 with which the periphery of the first cable bundle 116 is coated. The first shield layer 118 can be made of an insulating film obtained by laminating metallic foils through an adhesive. The insulating film is made of a polyethylene terephthalate (PET) film. The metallic foil is made of an aluminum foil or a copper foil.

The non-coaxial cable 110 is shielded by the first shield layer 118 with a plurality of signal wires 112 as one set. The signal wires 112 are handled in a unit of the non-coaxial cable 110.

As shown in FIG. 4, in the non-coaxial cable 110 of the embodiment, the first cable bundle 116 is configured by stranding seven wires in total of four signal wires 112 and three ground wires. One signal wire 112 of the four signal wires 112 is disposed at the center. The remaining three signal wires 112 and the three ground wires 114 are disposed adjacently in the periphery of the signal wire 112 at the center. Note that the number of signal wires 112, the number of ground wires 114, and the disposition of the wires in the first cable bundle 116 are not limited to the structure of FIG. 4.

Figure 5:
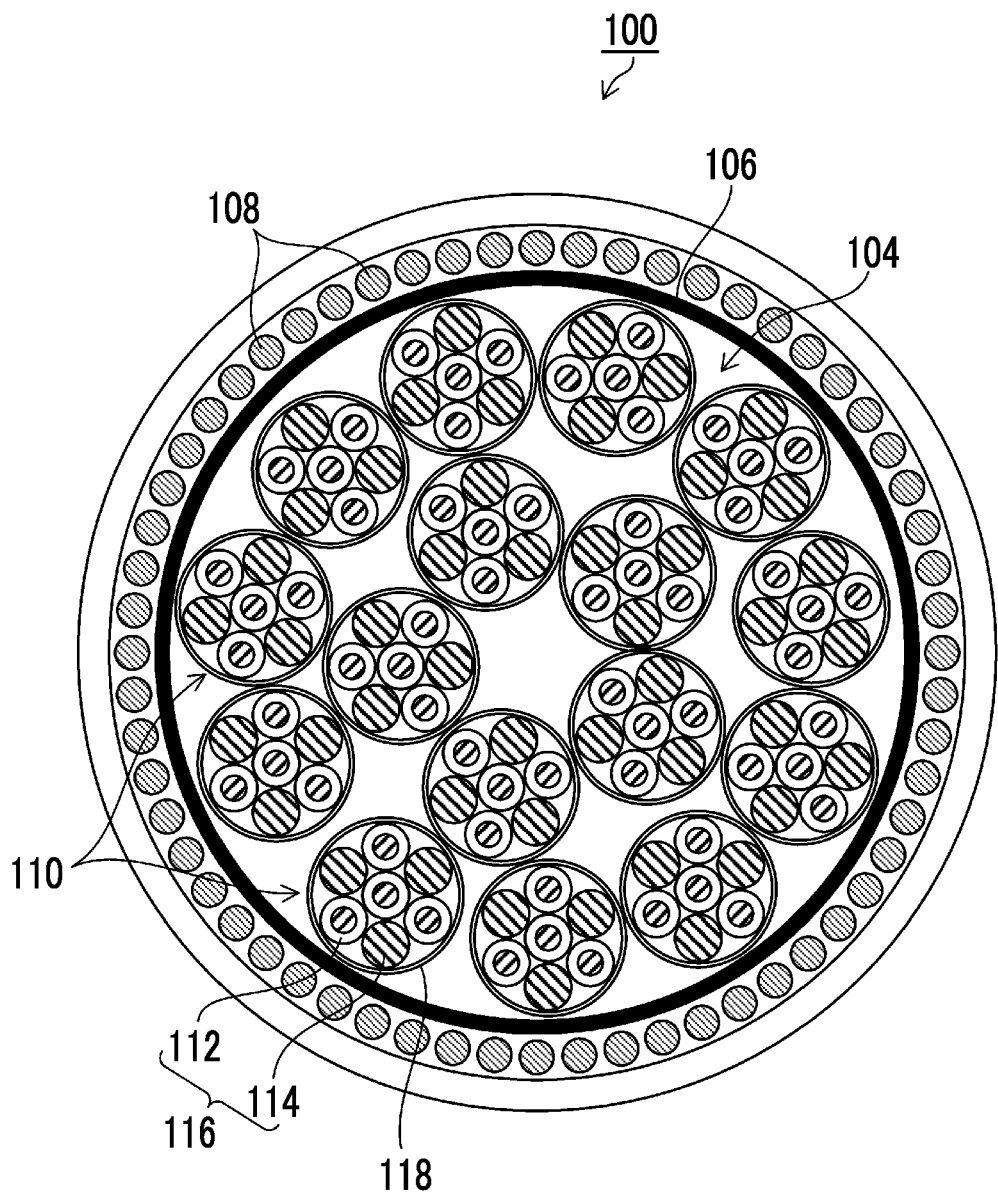
FIG. 5 is a sectional view of a cable.

As shown in FIG. 5, the cable 100 comprises a plurality of non-coaxial cables 110. A second cable bundle 104 is configured with a plurality of non-coaxial cables 110.

The second cable bundle 104 is coated with the outer coat 102. The outer coat 102 can be made of a fluorine-based resin material, such as extruded and coated PFA, FEP, an ethylene/ethylene tetrafluoride copolymer (ETFE), or polyvinyl chloride (PVC). The outer coat 102 can be made of a wound resin tape (PET tape). The coating of the second cable bundle 104 with the outer coat 102 includes a case where the outside of the second cable bundle 104 is coated directly and a case where the outside of the second cable bundle 104 is coated indirectly. Indirect coating includes disposing another layer between the outer coat 102 and the second cable bundle 104.

The cable 100 of the embodiment comprises, in order from the inside, a resin layer 106 and a second shield layer 108 between the outer coat 102 and the second cable bundle 104. The second cable bundle 104 is coated with the resin layer 106. The resin layer 106 can be made of, for example, the fluorine-based resin material or the resin tape described above.

The second shield layer 108 may be configured by, for example, braiding a plurality of element wires. The element wire is made of a copper wire, a copper alloy wire, or the like subjected to plating processing (tin plating or silver plating).

The cable 100 may not comprise both the resin layer 106 and the second shield layer 108 other than the above-described configuration or may comprise only one of the resin layer 106 or the second shield layer 108.

The cable 100 of the embodiment includes 16 non-coaxial cables 110, and includes 64 signal wires 112. The number of non-coaxial cables 110 and the number of signal wires 112 are not limited to the numerical values.

As described above, the non-coaxial cable 110 included in the cable 100 does not comprise a shield layer and an outer coat for each signal wire 112, unlike the coaxial cable in the related art. In particular, in a case where the cable 100 is configured with a plurality of non-coaxial cables 110, the cable 100 can be reduced in diameter compared to the coaxial cable in the related art. In a case where the outside diameter is the same as the outside diameter of the coaxial cable, the cable 100 can comprise a greater number of signal wires 112 than the coaxial cable in the related art.

Figure 6:
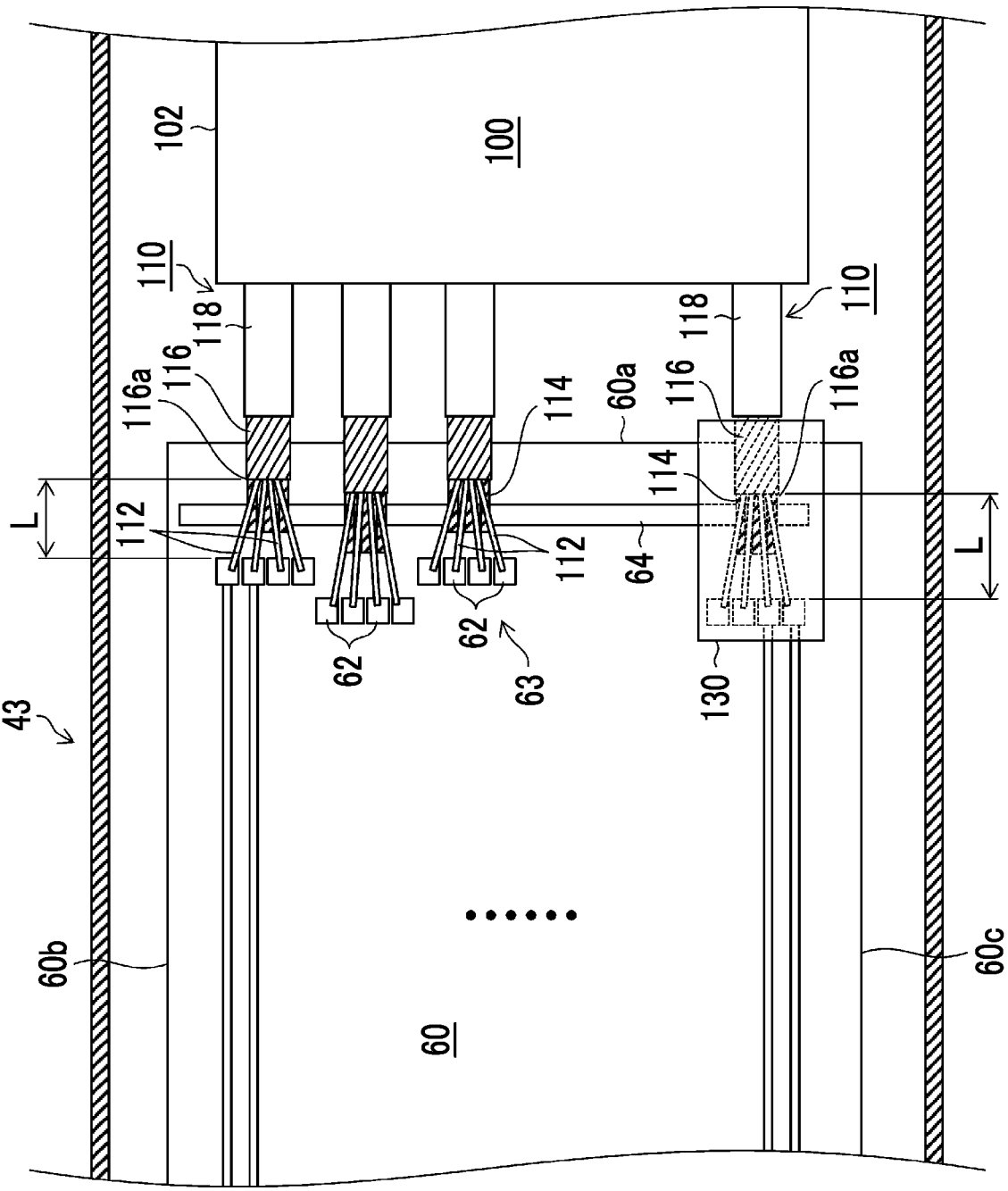
FIG. 6 is a diagram showing a first form of a connection structure of a flexible substrate and non-coaxial cables.

Next, a first form of a connection structure of the flexible substrate 60 and the non-coaxial cables 110 will be described. As shown in FIG. 6, on a side 60a of the flexible substrate 60, the resin layer 106 (not shown), the second shield layer 108 (not shown), and the outer coat 102 of the cable 100 are removed, and a plurality of non-coaxial cables 110 are exposed. On a side close to the side 60a of the flexible substrate 60, the first shield layer 118 of each non-coaxial cable 110 is removed, and the first cable bundle 116 is exposed. The non-coaxial cables 110 are disposed in parallel with a side 60b and a side 60c perpendicular to the side 60a.

The flexible substrate 60 and the first shield layer 118 do not overlap each other as viewed from a direction perpendicular to the principal surface of the flexible substrate 60 (hereinafter, referred to as plan view). The flexible substrate 60 and the first shield layer 118 may overlap each other.

The first cable bundle 116 configured with a stranded wire of a plurality of signal wires 112 and a plurality of ground wires 114 is unstranded into the respective signal wires 112 at a distal end 116a. The unstranded signal wires 112 are electrically bonded to the electrode pads 62 disposed on the flexible substrate 60, respectively, and a plurality of first electrical bonded portions 63 are formed. The distal end 116a is a start position where each signal wire 112 is unstranded.

In the connection structure of the first form shown in FIG. 6, the electrode pads 62 corresponding to each non-coaxial cable 110 are collectively disposed. That is, the first electrical bonded portions 63 of four signal wires 112 and four electrode pads 62 are collectively disposed on the flexible substrate 60 for each first cable bundle 116. This is to make a distance between the non-coaxial cable 110 and the electrode pads 62 short to avoid disconnection of the signal wires 112 of the non-coaxial cable 110.

In the embodiment, the flexible substrate 60 extends from the distal end part 40 to a part of the flexible part 43 while passing through the bending part 42, and the first electrical bonded portions 63 of the electrode pads 62 and the signal wires 112 are positioned on the flexible substrate 60 and in a region of the flexible part 43.

Electrical bonding of a plurality of non-coaxial cables 110 of the cable 100 and the flexible substrate 60 can be made even at positions of the distal end part 40 by extending the cable 100 to the distal end part 40 and reducing the size of the flexible substrate 60.

However, the distal end part 40 is intended to be inserted into a human body. For this reason, the distal end part 40 has a very small space, and the flexible substrate 60 that is disposed therein is also reduced in size. Since a structure is employed in which the electrode pads 62 corresponding to the non-coaxial cables 110 are collectively disposed, on the flexible substrate 60, the disposition of the electrode pads 62 is restricted and a degree of freedom of wirings of a plurality of non-coaxial cables 110 and the flexible substrate 60 is degraded.

Bending of the flexible part 43 is more moderate than bending of the bending part 42, and the flexible part 43 can increase by extending the flexible substrate 60 in the longitudinal axis direction. For this reason, a plurality of first electrical bonded portions 63 can be formed on the flexible substrate 60 and in the region of the flexible part 43. As a result, it is possible to increase the degree of freedom of wirings of the non-coaxial cables 110 and the flexible substrate 60 compared to a case where bonding is made in the distal end part 40.

It is preferable that the reinforcing material 130 that protects the first electrical bonded portions 63 is provided in the first electrical bonded portions 63 to prevent disconnection of the signal wires 112 even in a case where a large load is applied to the first electrical bonded portions 63. It is preferable that the reinforcing material 130 is a member having high rigidity (rigid). It is preferable that the reinforcing material 130 is an insulating resin layer by adhesive curing or the like, a metal, or a resin member having high hardness. In particular, in a case where the reinforcing material 130 is a metal, radiation electromagnetic waves can be suppressed. In some first cable bundles 116, the reinforcing material 130 is omitted for ease of understanding.

A ground electrode pad 64 is disposed on the flexible substrate 60 separately from the electrode pads 62. The ground wires 114 included in the first cable bundle 116 are electrically bonded to the ground electrode pad 64. The ground wires 114 are electrically bonded to the ground electrode pad 64, whereby the ground potentials of a plurality of first cable bundles 116 can be at the same potential. At least one ground wire 114 of a plurality of ground wires 114 may be electrically bonded to the ground electrode pad 64. This is because a plurality of ground wires 114 are in contact with each other in the first cable bundle 116. A region occupied by the wires can be reduced by reducing the number of ground wires 114 that are electrically bonded to the ground electrode pad 64.

In the connection structure shown in FIG. 6, the positions of the electrode pads 62 connected to the signal wires 112 of the non-coaxial cable 110 are different between adjacent non-coaxial cables 110. That is, in regard to a distance L between the distal end 116a of the first cable bundle 116 and the electrode pad 62, there are two kinds of different distances L (see the distance L on a side closer to the side 60b of FIG. 6 and the distance L on a side closer to the side 60c).

As a result, a plurality of electrode pads 62 corresponding to the signal wires 112 of the non-coaxial cable 110 are disposed in zigzags for every plurality of electrode pads 62 in plan view. It is possible to narrow an interval between a plurality of adjacent electrode pads 62, and to dispose a plurality of electrode pads 62 with high density compared to a case where a plurality of electrode pads 62 are not disposed in zigzags (a case where a plurality of electrode pads 62 are disposed linearly along the side 60*a*).

In FIG. 6, although the two kinds of distances L are shown, two kinds or more of distances L can be set. It is possible to dispose a plurality of electrode pads 62 with higher density.

The lengths of the signal wires 112 are different between the first cable bundles 116 of the non-coaxial cables 110 corresponding to the electrode pads 62 disposed in zigzags.

On the other hand, in a unit of the non-coaxial cables 110, the distance L between the electrode pads 62 corresponding to a plurality of signal wires 112 and the distal end 116*a* of the first cable bundle 116 are equal.

Figure 7:
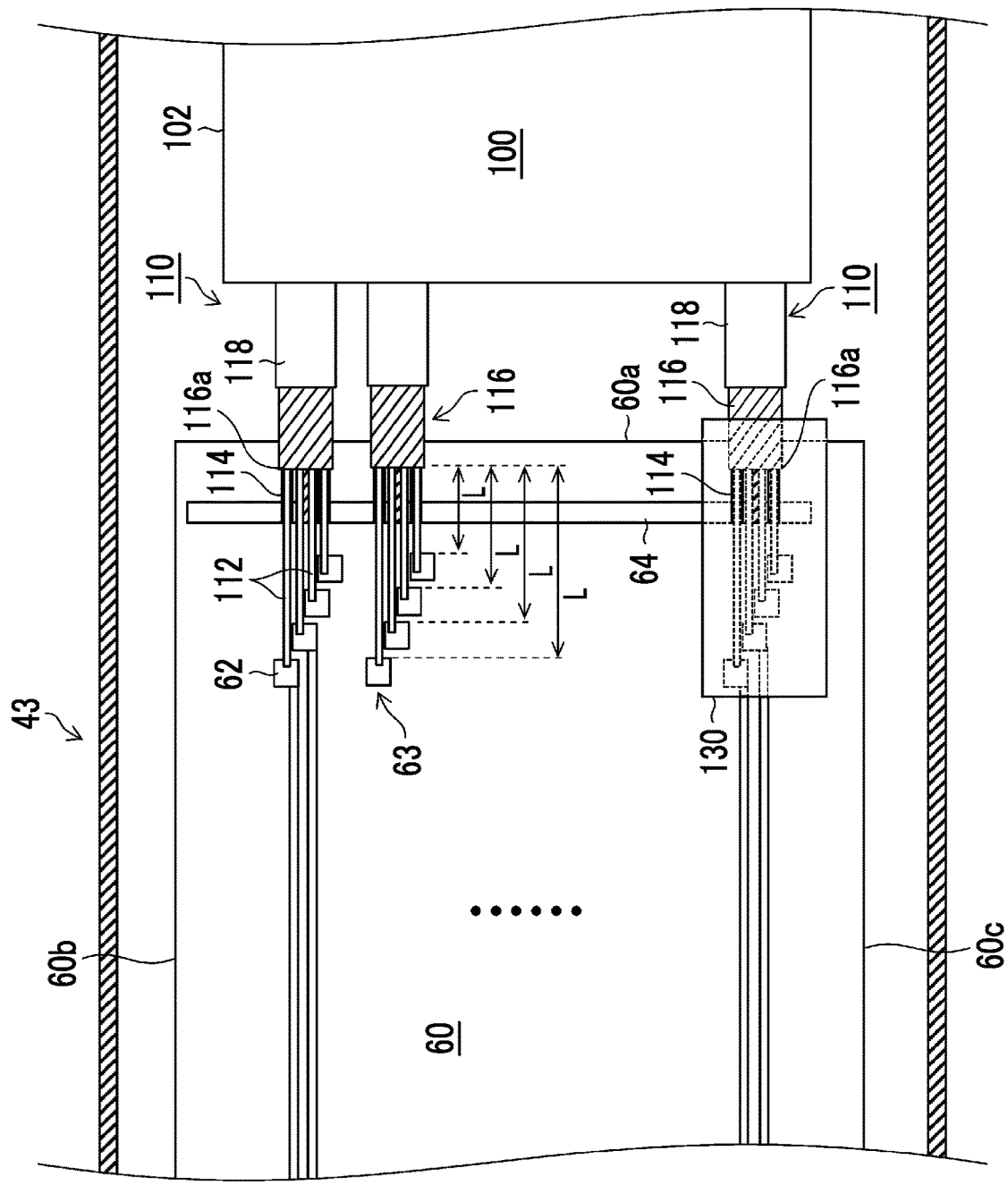
FIG. 7 is a diagram showing a second form of a connection structure of the flexible substrate and the non-coaxial cables.

Next, a second form of a connection structure of the flexible substrate 60 and the non-coaxial cables 110 will be described. The same configurations as the connection structure of FIG. 6 are represented by the same reference numerals, and description thereof may not be repeated. As shown in FIG. 7, on the proximal end side of the flexible substrate 60, the resin layer 106 (not shown), the second shield layer 108 (not shown), and the outer coat 102 of the cable 100 are removed, and a plurality of non-coaxial cables 110 are exposed. On the flexible substrate 60 side, the first shield layer 118 of each non-coaxial cable 110 is removed, and the first cable bundle 116 is exposed.

The non-coaxial cable 110 includes the first cable bundle 116 consisting of a plurality of signal wires 112 and a plurality of ground wires 114. For each first cable bundle 116, there are four kinds of distances L between the electrode pads 62 of the flexible substrate 60 corresponding to a plurality of signal wires 112 included in the first cable bundle 116 and the distal end 116*a* of the first cable bundle 116.

As a result, in plan view, a plurality of electrode pads 62 corresponding to the first cable bundle 116 are sequentially disposed shifted along the longitudinal axis direction (a direction along the side 60*b*) of the cable, an arrangement pitch of the electrode pads 62 in a direction (a direction along the side 60*a*) perpendicular to the longitudinal axis direction of the cable is made small, and a space occupied by the electrode pad 62 in the same direction is narrowed. It is possible to dispose a plurality of electrode pads 62 with high density for each first cable bundle 116. Even in the second form, the first electrical bonded portions 63 are formed on the flexible substrate 60 and in the region of the flexible part 43.

Figure 8:
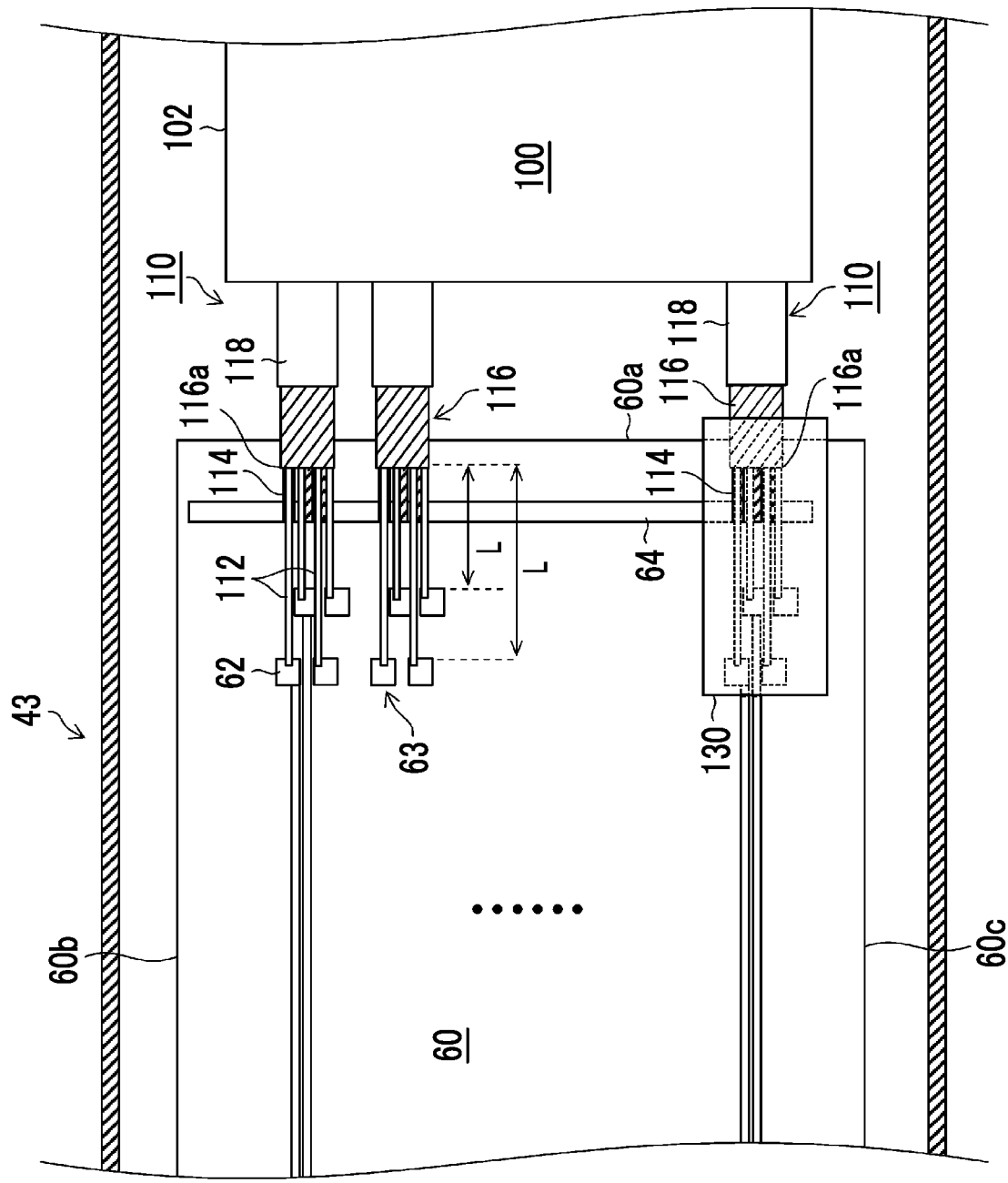
FIG. 8 is a diagram showing a modification of the second form of the connection structure of the flexible substrate and the non-coaxial cables.

Next, a modification example of the second form of the connection structure of the flexible substrate 60 and the non-coaxial cables 110 will be described. The same configurations as the connection structure of FIG. 7 are represented by the same reference numerals, and description thereof may not be repeated. As shown in FIG. 8, for each first cable bundle 116, there are two kinds of distances L between the electrode pads 62 of the flexible substrate 60 corresponding to a plurality of signal wires 112 included in each first cable bundle 116 and the distal end 116*a* of the first cable bundle 116. In the modification example of the second form, the number of kinds of distances L is different from that in the second form.

In the first cable bundle 116, the distance L is different between adjacent signal wires 112. Since the distance L is different between adjacent signal wires 112, the electrode pads 62 are disposed in zigzags in plan view. It is possible to narrow the interval between a plurality of adjacent electrode pads 62, and to dispose a plurality of electrode pads 62 for each first cable bundle 116 with high density compared to a case where a plurality of electrode pads 62 are not disposed in zigzags (a case where a plurality of electrode pads 62 are disposed linearly along the side 60*a*). Even in the modification example of the second form, the first electrical bonded portions 63 are formed on the flexible substrate 60 and in the region of the flexible part 43.

In the second form and the modification example of the second form, as in the first form, it is possible to increase the degree of freedom of wirings of the non-coaxial cables 110 and the flexible substrate 60. In the second form and the modification example of the second form, as in the first form, the first electrical bonded portions 63 are collectively disposed on the flexible substrate 60 for each first cable bundle 116.

Figure 9:
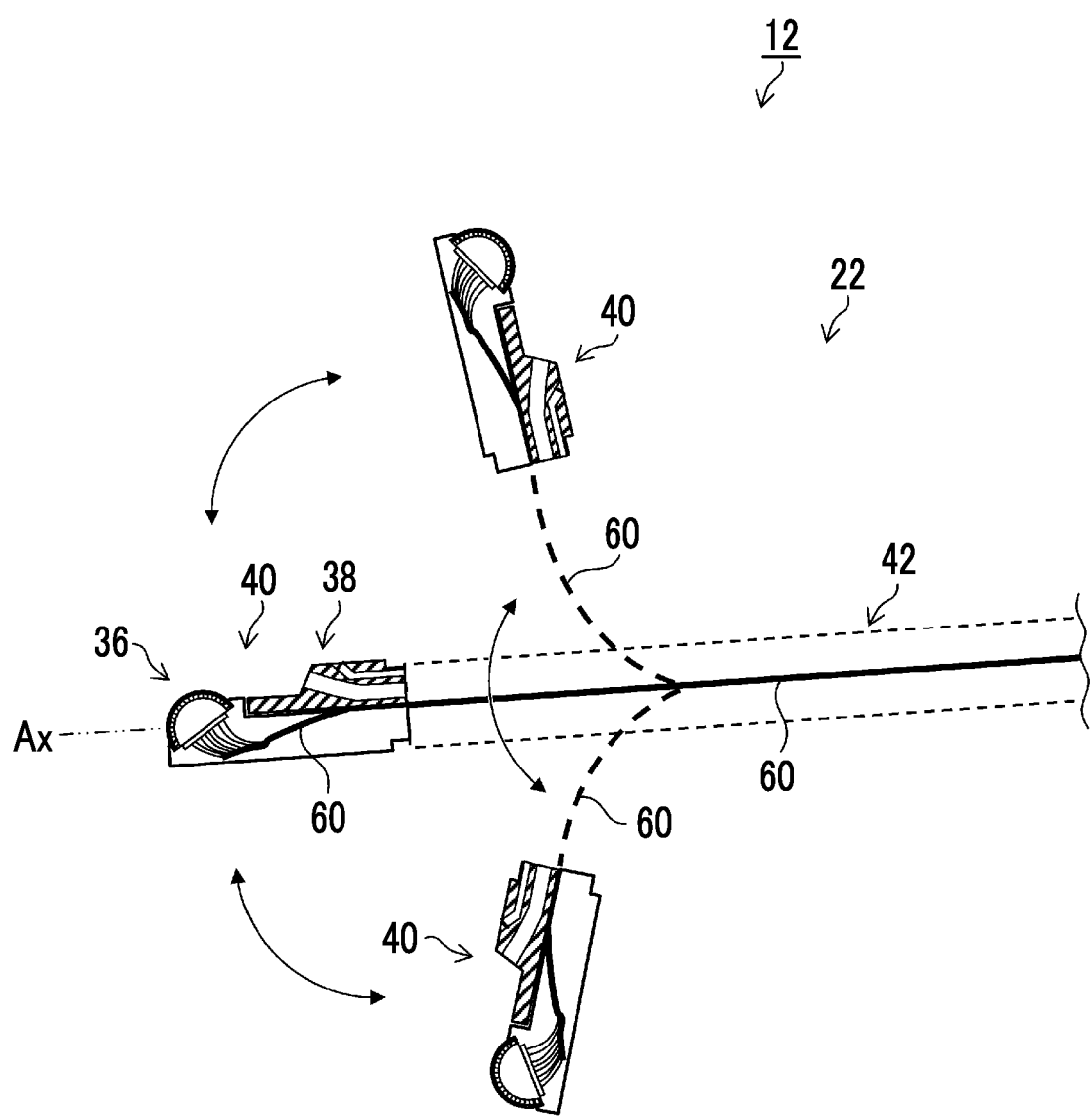
FIG. 9 is a diagram showing the operation of the bending part of the ultrasound bronchoscope.

FIG. 9 is a diagram showing the operation of the bending part of the ultrasound bronchoscope 12. As described above, in the ultrasound bronchoscope 12 of the embodiment, the flexible substrate 60 is disposed from the distal end part 40 to a part of the flexible part 43 while passing through the bending part 42, and is disposed to be bendable in the same two directions as the bending part 42. As shown in FIG. 9, the bending part 42 is bent in two directions by an operation of the angle lever 29 (not shown). That is, since the two principal surfaces of the flexible substrate 60 are disposed toward a bending direction of the bending part 42, the flexible substrate 60 follows the bending part 42 and is bendable in the same two directions.

In the embodiment, to reliably bend the flexible substrate 60 in the same two directions as the bending part 42, the distal end part 40 has a structure (hereinafter, referred to as a regulation structure) in which the rotation of the flexible substrate 60 with a longitudinal axis direction Ax of the insertion part 22 as a center of rotation is regulated.

Next, a preferred regulation structure will be described referring to the drawings. FIGS. 10A to 10C are diagrams illustrating a first form of a regulation structure. FIG. 10A is a plan view of the distal end part 40, FIG. 10B is a sectional view taken along a plane in parallel with the longitudinal axis direction Ax and perpendicular to the principal surface of the flexible substrate 60, and FIG. 10C is a sectional view taken along the line A1-A1.

As shown in FIG. 10B, the distal end part 40 is configured in a two-split structure of a first distal end member 40*a* and a second distal end member 40*b*. In the embodiment, the treatment tool lead-out port 44 and the observation window 82 are disposed in the first distal end member 40*a*. The ultrasound observation part 36, the signal wires 56, and a part of the flexible substrate 60 are disposed.

In FIG. 10A, for ease of understanding, the first distal end member 40*a* of the distal end part 40 is omitted. As shown in FIG. 10A, a groove 40*c* is formed on a proximal end side of the second distal end member 40*b*. The groove 40*c* extends linearly in parallel with the longitudinal axis direction Ax, and a part of the flexible substrate 60 is formed to have a width substantially equal to a length in a width direction (lateral direction) of the groove 40*c*. The flexible substrate 60 is disposed in the groove 40*c*.

As shown in FIG. 10C, the flexible substrate 60 is accommodated in the groove 40*c*. The first distal end member 40*a* and the second distal end member 40*b* sandwich the flexible substrate 60. The flexible substrate 60 is brought into a state in which the periphery thereof is surrounded by the first distal end member 40*a* and the groove 40*c* of the second distal end member 40*b*. The regulation structure of the distal end part 40 regulates the rotation direction of the flexible substrate 60. As a result, as shown in FIG. 9, the bending part 42 and the flexible substrate 60 can be bent in the same two directions.

In a case of sandwiching the flexible substrate 60, the first distal end member 40a and the second distal end member 40b may be separated from the flexible substrate 60. As long as the rotation direction of the flexible substrate 60 can be regulated such that the bending part 42 and the flexible substrate 60 can be bent in the same two directions, the flexible substrate 60 may not be in close contact with the first distal end member 40a and the second distal end member 40b.

Figure 11A:
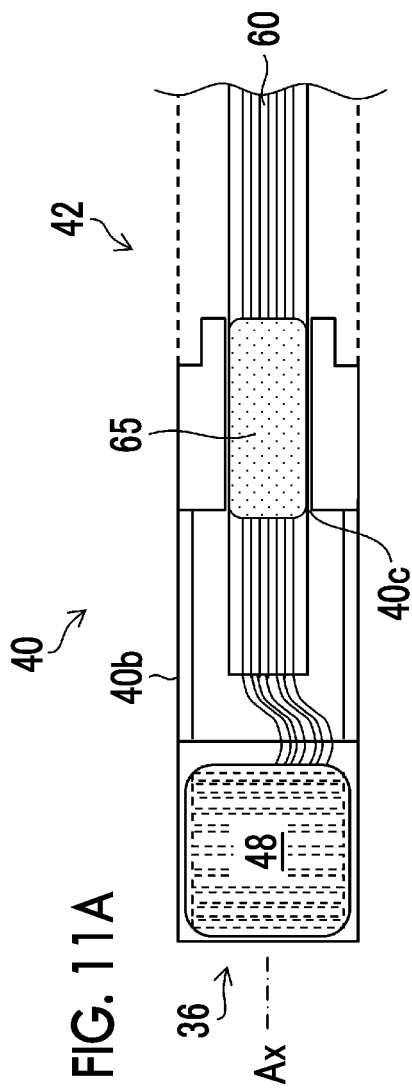
FIGS. 11A to 11C are diagrams illustrating a second form of a regulation structure.
Figure 11C:
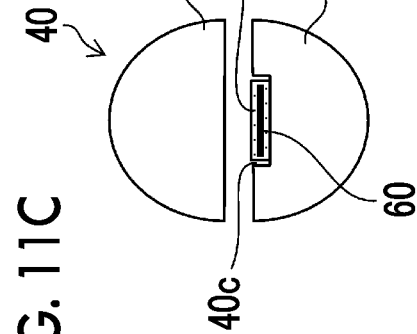
Figure 11B:
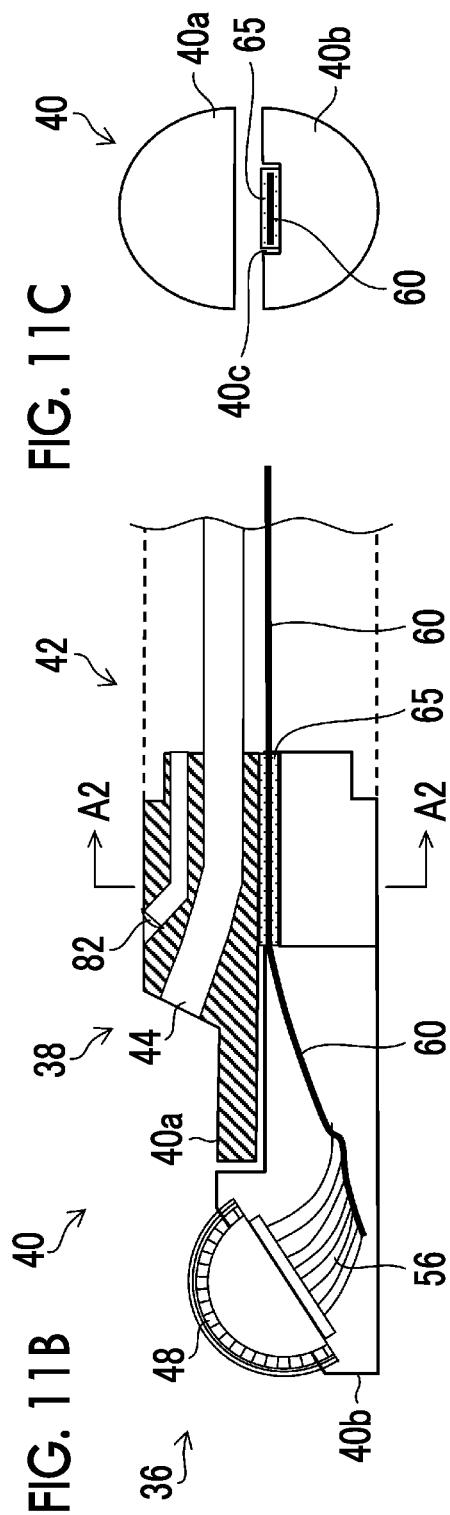

FIGS. 11A to 11C are diagrams illustrating a second form of a regulation structure. FIG. 11A is a plan view of the distal end part 40, FIG. 11B is a sectional view taken along a plane in parallel with the longitudinal axis direction Ax and perpendicular to the principal surface of the flexible substrate 60, and FIG. 11C is a sectional view taken along the line A2-A2. In FIG. 11A, for ease of understanding, the first distal end member 40a of the distal end part 40 is omitted.

The same configurations as those in the first form of the regulation structure are represented by the same reference numerals, and description thereof may not be repeated. The second form of the regulation structure is different from the first form of the regulation structure in that the flexible substrate 60 is coated with a sealing member 65 at a fixed position (groove 40c). A part of the flexible substrate 60 is fixed to the groove 40C of the second distal end member 40b by the sealing member 65. As the sealing member 65, a sealant, a sealing tape, or the like can be applied.

Figures 12A, 12B, 12C:
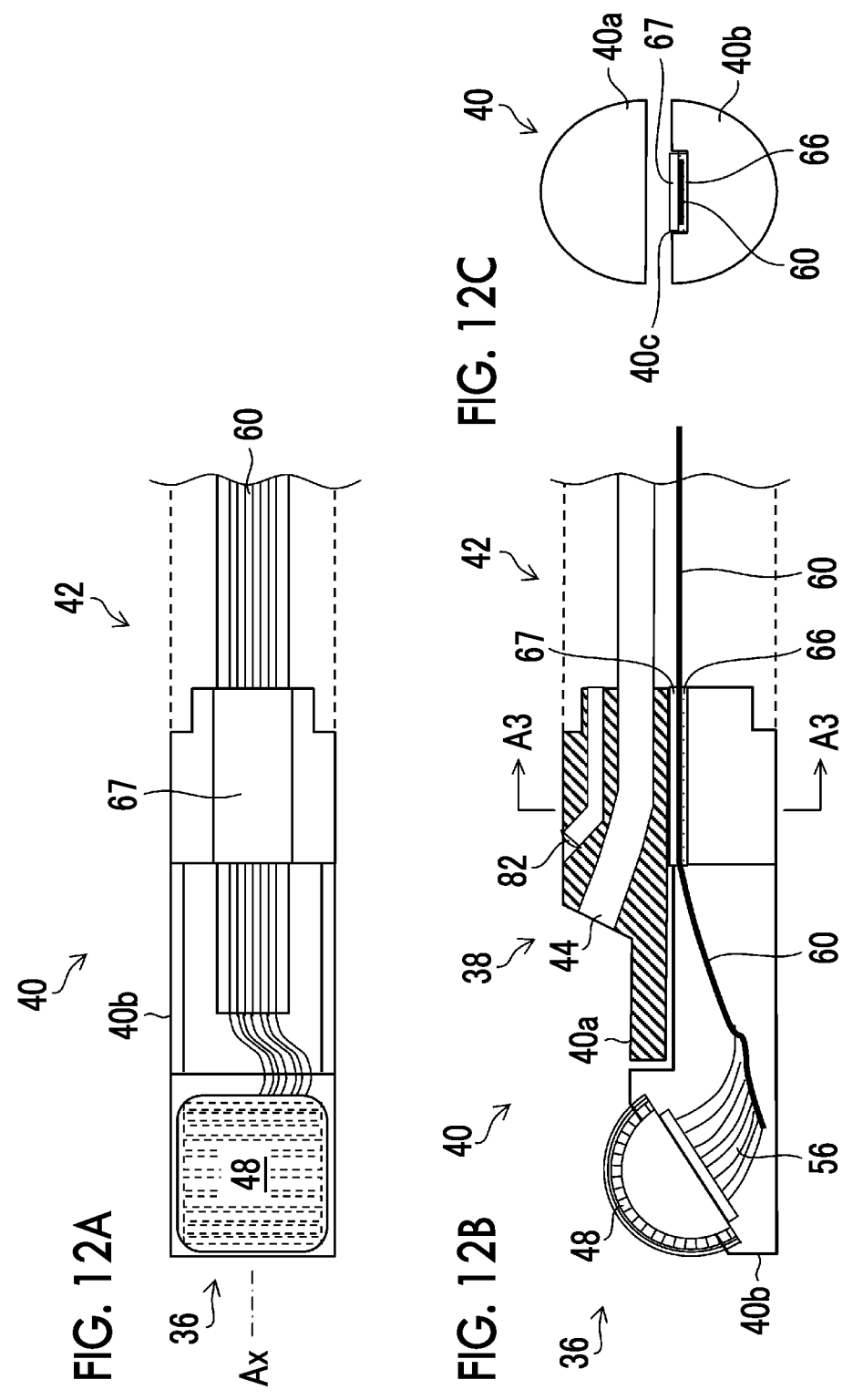

FIGS. 12A to 12C are diagrams illustrating a third form of a regulation structure. FIG. 12A is a plan view of the distal end part 40, FIG. 12B is a sectional view taken along a plane in parallel with the longitudinal axis direction Ax and perpendicular to the principal surface of the flexible substrate, and FIG. 12C is a sectional view taken along the line A3-A3. In FIG. 12A, for ease of understanding, the first distal end member 40a of the distal end part 40 is omitted.

The same configurations as those in the first form and the second form of the regulation structure are represented by the same reference numerals, and description thereof may not be repeated. The third form of the regulation structure is different from the first form and the second form of the regulation structure in that a part of the flexible substrate 60 is fixed to the groove 40c of the second distal end member 40b by an adhesive 66. A cover member 67 different from the first distal end member 40a and the second distal end member 40b sandwich the flexible substrate 60. In the third form of the regulation structure, the flexible substrate 60 is fixed to the groove 40c by the cover member 67 and the adhesive 66.

FIGS. 13A to 13C are diagrams illustrating a fourth form of a regulation structure. FIG. 13A is an enlarged plan view of the distal end part, FIG. 13B is a sectional view taken along a plane in parallel with the longitudinal axis direction Ax and perpendicular to the principal surface of the flexible substrate, and FIG. 13C is a sectional view taken along the line A4-A4. In FIG. 13A, for ease of understanding, the first distal end member 40a of the distal end part 40 is omitted.

The same configurations at those in the first form to the third form of the regulation structure are represented by the same reference numerals, and description thereof may not be repeated. The fourth form of the regulation structure is not different from the first form to the third form of the regulation structure in that the second distal end member 40b is provided with a through-hole 40d extending along the longitudinal axis direction Ax. The through-hole 40d has openings through which the flexible substrate 60 can be inserted, on a proximal end side and a distal end side. The flexible substrate 60 is inserted into the through-hole 40d of the second distal end member 40b. A locking member 68 is inserted into a gap between the through-hole 40d and the flexible substrate 60. In the fourth form of the regulation structure, the flexible substrate 60 is fixed to the through-hole 40d by the locking member 68.

Figures 14A, 14B, 14C:
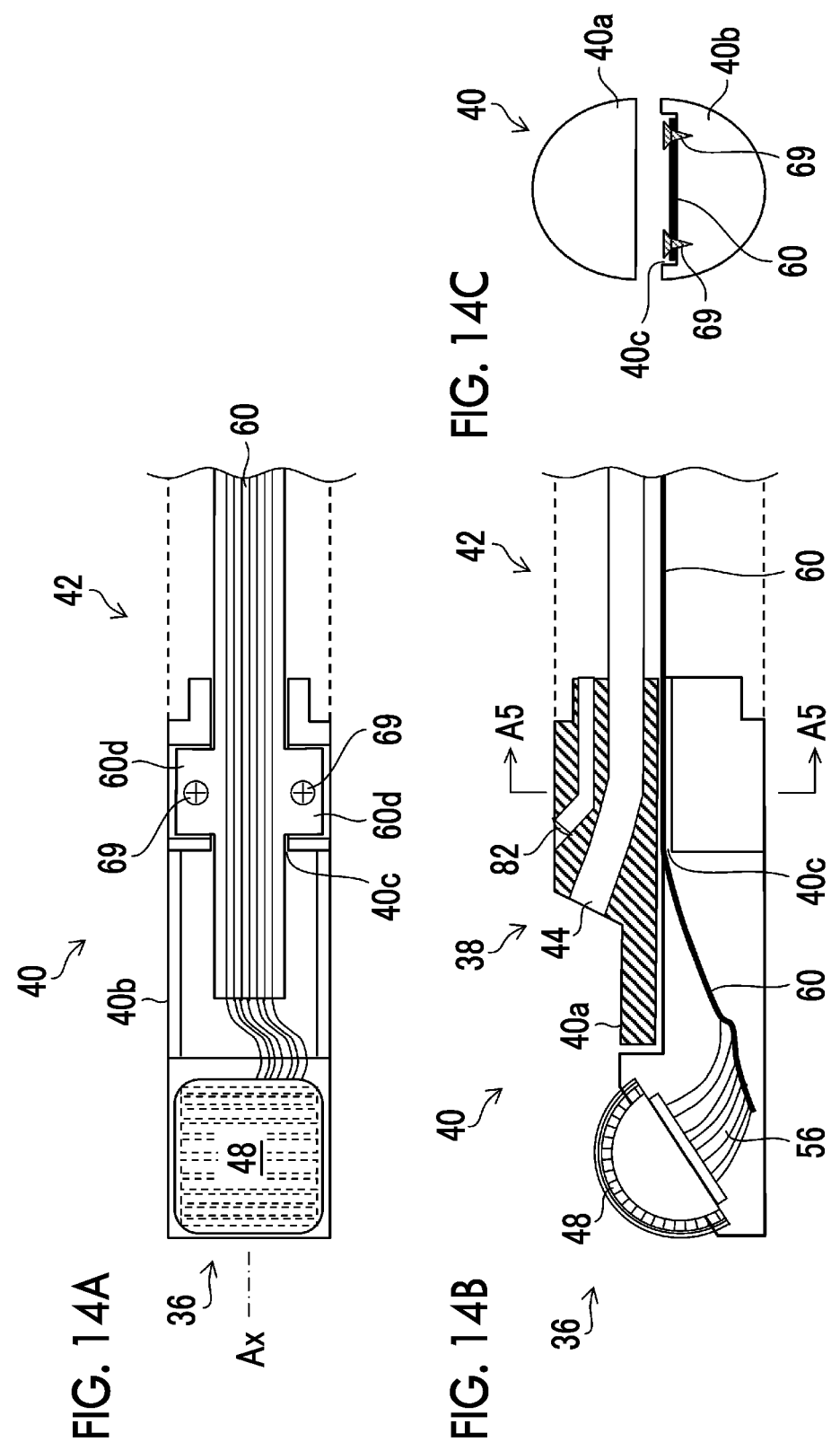

FIGS. 14A to 14C are diagrams illustrating a fifth form of a regulation structure. FIG. 14A is an enlarged plan view of the distal end part, FIG. 14B is a sectional view taken along a plane in parallel with the longitudinal axis direction Ax and perpendicular to the principal surface of the flexible substrate, and FIG. 14C is a sectional view taken along the line A5-A5. In FIG. 14A, for ease of understanding, the first distal end member 40a of the distal end part 40 is omitted.

The same configurations as those in the first form to the fourth form of the regulation structure are represented by the same reference numerals, and description thereof may not be repeated. The fifth form of the regulation structure is different from the first form to the fourth form of the regulation structure in that the flexible substrate 60 is provided with two enlarged portions 60d extending in a width direction of the flexible substrate 60 and having a rectangular shape in plan view. A part and the enlarged portions 60d of the flexible substrate 60 are accommodated in a groove 40c of the second distal end member 40b. The groove 40c has a portion parallel to the longitudinal axis direction Ax and a portion perpendicular to the longitudinal axis direction Ax. The two enlarged portions 60d are accommodated in the portion of the groove 40c perpendicular to the longitudinal axis direction Ax. The two enlarged portions 60d are fixed to the groove 40c of the second distal end member 40b by screws that are fastening members 69.

Next, a connection structure of the cable and a connector substrate will be described referring to FIG. 15. The cable 100 is electrically connected to the electrode pads 62 of the flexible substrate 60 on the distal end side, and is electrically connected to a connector substrate 140 disposed in the ultrasound connector 32a on a rear end side.

On a side closer to a side 140a of the connector substrate 140, the first shield layer 118 of each non-coaxial cable 110 is removed, and the first cable bundle 116 is exposed. The non-coaxial cable 110 is disposed in parallel with a side 140b and a side 140c perpendicular to the side 140a. The connector substrate 140 comprises connector-side electrode pads 142 corresponding to the signal wires 112 included in the first cable bundle 116 of the non-coaxial cable 110. The signal wires 112 of the non-coaxial cable 110 and the connector-side electrode pads 142 are electrically bonded, and second electrical bonded portions 143 are formed. A plurality of second electrical bonded portions 143 are collectively disposed for each first cable bundle 116.

The first electrical bonded portions 63 are collectively disposed on the flexible substrate 60 for each first cable bundle 116, the second electrical bonded portions 143 are collectively disposed on the connector substrate 140 for each first cable bundle 116, and the first electrical bonded portions 63 and the second electrical bonded portions 143 are electrically connected in a one-to-one correspondence relationship.

As long as the first electrical bonded portions 63 and the second electrical bonded portions 143 have the above-described connection structures, an arrangement order of the corresponding first electrical bonded portions 63 and second electrical bonded portions 143 having the one-to-one correspondence relationship is not limited.

For example, the numbers of wirings that are connected to the electrode pads 62 corresponding to the first cable bundle 116 closest to the side 60*b* of the flexible substrate 60 are denoted as W1, W2, W3, and W4. W1, W2, W3, and W4 are connected to the corresponding ultrasound transducer 48 in the distal end part 40. The four signal wires 112 of the first cable bundle 116 are bonded to the electrode pads 62 corresponding to W1, W2, W3, and W4.

To transmit and receive ultrasound signals from and to W1, W2, W3, and W4 through the four signal wires 112, the signal wires 112 of the first cable bundle 116 are electrically bonded to the corresponding connector-side electrode pads 142.

As shown in FIG. 15, the arrangement order of the first electrical bonded portions 63 on the flexible substrate 60 may be different from the arrangement order of the second electrical bonded portions 143 on the connector substrate 140. The first electrical bonded portions 63 corresponding to W1, W2, W3, and W4 are positioned on the side 60*b*. On the other hand, the second electrical bonded portions 143 corresponding to W1, W2, W3, and W4 are positioned on the side 140*c*. As shown in FIG. 15, even in a case where the arrangement order of W1, W2, W3, and W4 is different between the flexible substrate 60 and the connector substrate 140, the first electrical bonded portions 63 and the second electrical bonded portion 143 corresponding to the first cable bundle 116 may be collectively disposed and may be electrically connected in the one-to-one correspondence relationship.

Figure 16A:
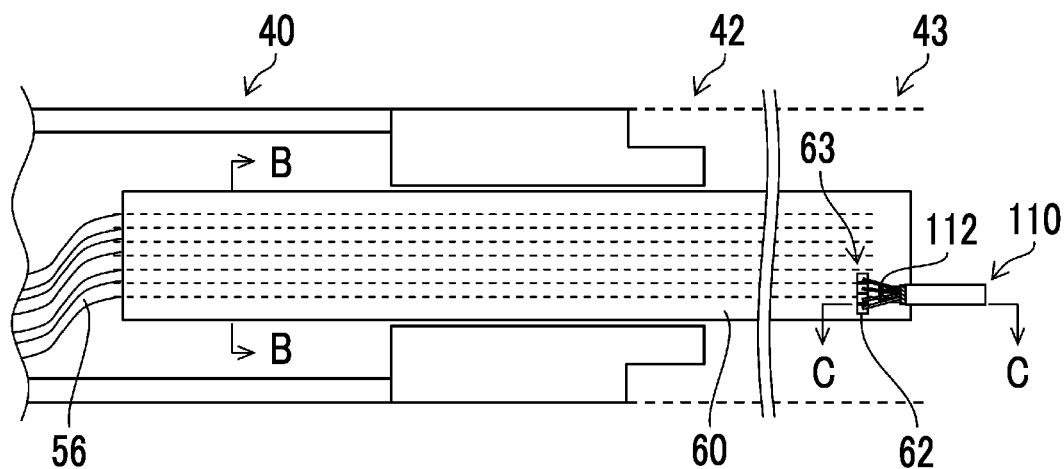
FIGS. 16A to 16C are diagrams illustrating an insulating member.
Figure 16B:
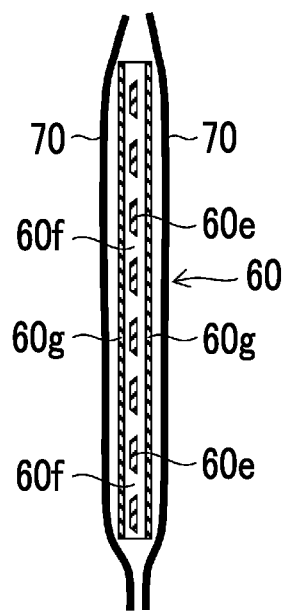
Figure 16C:
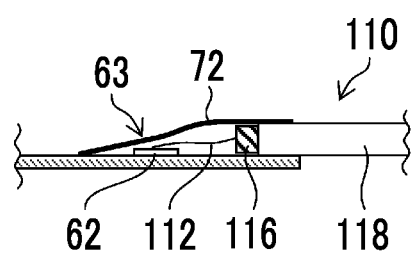

Next, a preferred form of the flexible substrate will be described referring to FIGS. 16A to 16C. FIG. 16A is a plan view of the flexible substrate 60, FIG. 16B is a sectional view taken along the line B-B, and FIG. 16C is a sectional view taken along the line C-C. In FIG. 16C, the sectional structure of the flexible substrate 60 is omitted. As shown in FIG. 16B, the flexible substrate 60 is configured with a multilayer flexible substrate comprising a plurality of signal wirings 60*e*, an insulating layer 60*f* that sandwiches the signal wirings 60*e*, and ground layers 60*g* provides on both surfaces of the insulating layer 60*f*. As the multilayer flexible substrate having a configuration in which the ground layers 60*g* on both surfaces sandwich the signal wirings 60*e* is employed, it is possible to reduce an influence of radiation electromagnetic waves on the flexible substrate 60. As the multilayer flexible substrate is employed, while the flexibility of the flexible substrate 60 is degraded, the multilayer flexible substrate can also be bent in two directions as long as the ultrasound bronchoscope 12 is bent in two directions.

As shown in FIG. 16B, since the ultrasound transducers 48 (not shown) are driven with a high voltage of about 40 V, to increase electrical safety, it is preferable that the flexible substrate 60 is covered with insulating members 70 (second insulating member). The insulating members 70 are, for example, an insulating tape. The flexible substrate 60 can be sandwiched by the insulating members 70 from both sides. An insulating tube other than the insulating tape can be applied as the insulating members 70. It is preferable that the insulating members 70 have a dielectric breakdown voltage equal to or greater than 2 kV.

As shown in FIG. 16C, it is preferable that the first electrical bonded portions 63 are covered with an insulating member 72. This is to increase safety similarly to FIG. 16B. The insulating member 72 (first insulating member) is an insulating tape or an insulating tube. It is preferable that the insulating member 72 has a characteristic of a dielectric breakdown voltage equal to or greater than 2 kV.

Although the invention has been described, the invention is not limited to the above-described example, and various improvements or modifications may be of course made without departing from the spirit and scope of the invention.

EXPLANATION OF REFERENCES

10: ultrasonography system
12: ultrasound bronchoscope
14: ultrasound processor device
16: endoscope processor device
18: light source device
20: monitor
21: suction pump
22: insertion part
24: operating part
26: universal cord
27: balloon water supply port
28*a*: suction button
28*b*: suction connector
29: angle lever
30: treatment tool insertion port
32*a*: connector
32*b*: connector
32*c*: connector
34: suction tube
36: ultrasound observation part
38: endoscope observation part
40: distal end part
40*a*: first distal end member
40*b*: second distal end member
40*c*: groove
40*d*: through-hole
41: exterior member
42: bending part
43: flexible part
44: treatment tool lead-out port
45: treatment tool channel
46: ultrasound transducer unit
47: laminate
48: ultrasound transducer
50: ultrasound transducer array
54: backing material layer
56: signal wire
60: flexible substrate
60*a*: side
60*b*: side
60*c*: side
60*d*: enlarged portion
60*e*: signal wiring
60*f*: insulating layer
60*g*: ground layer
62: electrode pad
63: first electrical bonded portion
64: ground electrode pad
65: sealing member
66: adhesive
67: cover member
68: locking member
69: fastening member
70: insulating member
72: insulating member
76: acoustic matching layer
78: acoustic lens
82: observation window
88: illumination window
100: cable 102: outer coat
104: second cable bundle
106: resin layer
108: second shield layer
110: non-coaxial cable
112: signal wire
112a: conductor
112b: insulating layer
114: ground wire
116: first cable bundle
116a: distal end
118: first shield layer
130: reinforcing material
140: connector substrate
140a: side
140b: side
140c: side
142: connector-side electrode pad
143: second electrical bonded portion
Ax: longitudinal axis direction
L: distance

What is claimed is:

1. An ultrasound bronchoscope comprising:
a distal end part that has an ultrasound transducer array in which a plurality of ultrasound transducers are arranged;
a bending part that is coupled to a proximal end of the distal end part and is bendable in two directions;
a flexible part that is coupled to a proximal end of the bending part;
a cable that is inserted into the flexible part; and
a flexible substrate that electrically connects the plurality of ultrasound transducers and the cable, and includes a plurality of electrode pads connected to the plurality of ultrasound transducers, respectively,
wherein the cable has:
a plurality of non-coaxial cables each of which includes a first cable bundle including a plurality of signal wires and a plurality of ground wires, and a first shield layer which coats the first cable bundle; and
an outer coat which coats the plurality of non-coaxial cables,
the flexible substrate extends from the distal end part through the bending part into the flexible part,
the distal end part has a structure for regulating a rotation direction of the flexible substrate, such that the flexible substrate is bendable in the same two directions as the bending part,
in the flexible part, the signal wires led out from each first cable bundle are electrically bonded to the electrode pads in a plurality of first electrical bonded portions on the flexible substrate.

2. The ultrasound bronchoscope according to claim 1, wherein the plurality of first electrical bonded portions are collectively disposed for each first cable bundle,
the cable is connected to a connector substrate on a proximal end side,
the connector substrate includes connector-side electrode pads corresponding to the signal wires included in the first cable bundle,
the connector-side electrode pads and the signal wires are connected to form a plurality of second electrical bonded portions, and
the plurality of second electrical bonded portions are collectively disposed for each first cable bundle.

3. The ultrasound bronchoscope according to claim 1, wherein the flexible substrate is a multilayer flexible substrate with ground layers respectively provided on both surfaces.

4. The ultrasound bronchoscope according to claim 1, further comprising:
a first insulating member that covers the first electrical bonded portions.

5. The ultrasound bronchoscope according to claim 1, further comprising:
a second insulating member that covers the flexible substrate.

6. The ultrasound bronchoscope according to claim 1, further comprising:
a reinforcing material that protects the first electrical bonded portions.

7. The ultrasound bronchoscope according to claim 1, wherein the structure is configured with, as the distal end part has a two-split structure of a first distal end member and a second distal end member, the flexible substrate fixed to a groove of the second distal end member by an adhesive, and the first distal end member and the second distal end member that sandwich the flexible substrate.

8. The ultrasound bronchoscope according to claim 1, wherein the structure is configured with, as the distal end part has a two-split structure of a first distal end member and a second distal end member, the flexible substrate coated with a sealing member and fixed to a groove of the second distal end member by the sealing member, and the first distal end member and the second distal end member that sandwich the flexible substrate.

9. The ultrasound bronchoscope according to claim 1, wherein the structure is configured with, the distal end part has a two-split structure of a first distal end member and a second distal end member, the flexible substrate fixed to a groove of the second distal end member by an adhesive, and a cover member different from the first distal end member and the second distal end member that sandwich the flexible substrate.

10. The ultrasound bronchoscope according to claim 1, wherein the structure is configured with, the distal end part has a two-split structure of a first distal end member and a second distal end member, the flexible substrate inserted into a through-hole provided in the second distal end member, and a locking member inserted into a gap with the flexible substrate in the through-hole.

11. The ultrasound bronchoscope according to claim 1, wherein the structure is a structure in which, as the distal end part has a two-split structure of a first distal end member and a second distal end member, the flexible substrate is disposed in a groove of the second distal end member, and the flexible substrate is fixed to the second distal end member by a fastening member.

12. The ultrasound bronchoscope according to claim 1, wherein, on the flexible substrate, the plurality of the first electrical bonded portions are disposed at two or more positions in a direction of a longitudinal axis of the flexible part.

* * * * *